United States Patent
Estes et al.

(10) Patent No.: US 11,892,426 B2
(45) Date of Patent: Feb. 6, 2024

(54) DEVICES, SYSTEMS, AND METHODS TO COMPENSATE FOR EFFECTS OF TEMPERATURE ON IMPLANTABLE SENSORS

(71) Applicant: DexCom, Inc., San Diego, CA (US)

(72) Inventors: Michael J. Estes, Poway, CA (US); Jennifer Blackwell, San Diego, CA (US); Sebastian Bohm, San Diego, CA (US); Robert J. Boock, Carlsbad, CA (US); Jack Pryor, Ladera Ranch, CA (US); Peter C. Simpson, Cardiff, CA (US); Matthew D. Wightlin, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 194 days.

(21) Appl. No.: 17/163,083

(22) Filed: Jan. 29, 2021

(65) Prior Publication Data
US 2021/0231602 A1    Jul. 29, 2021

Related U.S. Application Data

(63) Continuation of application No. 14/567,293, filed on Dec. 11, 2014, now Pat. No. 10,908,114, which is a (Continued)

(51) Int. Cl.
*G01N 27/403* (2006.01)
*A61B 5/145* (2006.01)
(Continued)

(52) U.S. Cl.
CPC ......... *G01N 27/403* (2013.01); *A61B 5/1495* (2013.01); *A61B 5/14532* (2013.01); *A61B 5/14865* (2013.01)

(58) Field of Classification Search
CPC .................................................. A61B 5/14532
See application file for complete search history.

(56) References Cited

U.S. PATENT DOCUMENTS

| 65,604 A | 6/1867 | Reynolds |
| 4,757,022 A | 7/1988 | Shults et al. |

(Continued)

FOREIGN PATENT DOCUMENTS

WO    WO-2012174563 A1    12/2012

OTHER PUBLICATIONS

Summons to Oral Proceedings pursuant to Rule 115 (1) EPC for European Application No. 13735148.2, dated Apr. 1, 2021, 3 pages.
(Continued)

*Primary Examiner* — Puya Agahi
(74) *Attorney, Agent, or Firm* — Schwegman Lundberg & Woessner, P.A.

(57) ABSTRACT

Systems and methods for compensating for effects of temperature on implantable sensors are provided. In some embodiments, systems and methods are provided for measuring a temperature to determine a change in temperature in a sensor environment. In certain embodiments, a temperature compensation factor is determined based on a change in temperature of the sensor environment. The temperature compensation factor can be used in processing raw data of an analyte signal to report a more accurate analyte concentration.

21 Claims, 20 Drawing Sheets

Related U.S. Application Data continuation of application No. 13/747,746, filed on Jan. 23, 2013, now Pat. No. 10,598,627.

(60) Provisional application No. 61/666,618, filed on Jun. 29, 2012.

(51) Int. Cl.
*A61B 5/1486* (2006.01)
*A61B 5/1495* (2006.01)

(56) References Cited

U.S. PATENT DOCUMENTS

| | | | |
|---|---|---|---|
| 4,787,398 A | 11/1988 | Garcia et al. |
| 4,994,167 A | 2/1991 | Shults et al. |
| 5,497,772 A | 3/1996 | Schulman et al. |
| 6,001,067 A | 12/1999 | Shults et al. |
| 6,558,321 B1 | 5/2003 | Burd et al. |
| 6,558,351 B1 | 5/2003 | Steil et al. |
| 6,666,821 B2 | 12/2003 | Keimel |
| 6,702,857 B2 | 3/2004 | Brauker et al. |
| 6,741,877 B1 | 5/2004 | Shults et al. |
| 6,770,030 B1 | 8/2004 | Schaupp et al. |
| 6,809,653 B1 | 10/2004 | Mann et al. |
| 6,862,465 B2 | 3/2005 | Shults et al. |
| 6,918,874 B1 | 7/2005 | Hatch et al. |
| 6,931,327 B2 | 8/2005 | Goode, Jr. et al. |
| 7,074,307 B2 | 7/2006 | Simpson et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,192,450 B2 | 3/2007 | Brauker et al. |
| 7,226,978 B2 | 6/2007 | Tapsak et al. |
| 7,276,029 B2 | 10/2007 | Goode, Jr. et al. |
| 7,310,544 B2 | 12/2007 | Brister et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,761,130 B2 | 7/2010 | Simpson et al. |
| 7,771,352 B2 | 8/2010 | Shults et al. |
| 7,774,145 B2 | 8/2010 | Brauker et al. |
| 7,775,975 B2 | 8/2010 | Brister et al. |
| 7,778,680 B2 | 8/2010 | Goode, Jr. et al. |
| 7,783,333 B2 | 8/2010 | Brister et al. |
| 7,792,562 B2 | 9/2010 | Shults et al. |
| 7,797,028 B2 | 9/2010 | Goode, Jr. et al. |
| 7,826,981 B2 | 11/2010 | Goode, Jr. et al. |
| 7,828,728 B2 | 11/2010 | Boock et al. |
| 7,831,287 B2 | 11/2010 | Brister et al. |
| 7,835,777 B2 | 11/2010 | Shults et al. |
| 7,857,760 B2 | 12/2010 | Brister et al. |
| 7,860,545 B2 | 12/2010 | Shults et al. |
| 7,875,293 B2 | 1/2011 | Shults et al. |
| 7,881,763 B2 | 2/2011 | Brauker et al. |
| 7,885,697 B2 | 2/2011 | Brister et al. |
| 7,896,809 B2 | 3/2011 | Simpson et al. |
| 7,899,511 B2 | 3/2011 | Shults et al. |
| 7,901,354 B2 | 3/2011 | Shults et al. |
| 7,905,833 B2 | 3/2011 | Brister et al. |
| 7,914,450 B2 | 3/2011 | Goode, Jr. et al. |
| 7,917,186 B2 | 3/2011 | Kamath et al. |
| 7,920,906 B2 | 4/2011 | Goode, Jr. et al. |
| 7,925,321 B2 | 4/2011 | Goode, Jr. et al. |
| 7,927,274 B2 | 4/2011 | Rasdal et al. |
| 7,933,639 B2 | 4/2011 | Goode et al. |
| 7,935,057 B2 | 5/2011 | Goode, Jr. et al. |
| 7,946,984 B2 | 5/2011 | Brister et al. |
| 7,949,381 B2 | 5/2011 | Brister et al. |
| 7,955,261 B2 | 6/2011 | Goode et al. |
| 7,959,569 B2 | 6/2011 | Goode et al. |
| 7,970,448 B2 | 6/2011 | Shults et al. |
| 7,974,672 B2 | 7/2011 | Shults et al. |
| 7,976,492 B2 | 7/2011 | Brauker et al. |
| 7,979,104 B2 | 7/2011 | Kamath et al. |
| 7,986,986 B2 | 7/2011 | Goode et al. |
| 7,998,071 B2 | 8/2011 | Goode, Jr. et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,050,731 B2 | 11/2011 | Tapsak et al. |
| 8,052,601 B2 | 11/2011 | Goode, Jr. et al. |
| 8,053,018 B2 | 11/2011 | Tapsak et al. |
| 8,060,173 B2 | 11/2011 | Goode, Jr. et al. |
| 8,060,174 B2 | 11/2011 | Simpson et al. |
| 8,064,977 B2 | 11/2011 | Boock et al. |
| 8,073,519 B2 | 12/2011 | Goode, Jr. et al. |
| 8,073,520 B2 | 12/2011 | Kamath et al. |
| 8,116,840 B2 | 2/2012 | Feldman et al. |
| 8,118,877 B2 | 2/2012 | Brauker et al. |
| 8,128,562 B2 | 3/2012 | Goode, Jr. et al. |
| 8,133,178 B2 | 3/2012 | Brauker et al. |
| 8,150,488 B2 | 4/2012 | Goode, Jr. et al. |
| 8,155,723 B2 | 4/2012 | Shults et al. |
| 8,160,669 B2 | 4/2012 | Brauker et al. |
| 8,160,671 B2 | 4/2012 | Kamath et al. |
| 8,167,801 B2 | 5/2012 | Goode, Jr. et al. |
| 8,170,803 B2 | 5/2012 | Kamath et al. |
| 8,195,265 B2 | 6/2012 | Goode, Jr. et al. |
| 8,206,297 B2 | 6/2012 | Kamath et al. |
| 8,216,139 B2 | 7/2012 | Brauker et al. |
| 8,229,534 B2 | 7/2012 | Brister et al. |
| 8,229,535 B2 | 7/2012 | Mensinger et al. |
| 8,229,536 B2 | 7/2012 | Goode, Jr. et al. |
| 8,231,531 B2 | 7/2012 | Brister et al. |
| 8,233,958 B2 | 7/2012 | Brauker et al. |
| 8,233,959 B2 | 7/2012 | Kamath et al. |
| 8,249,684 B2 | 8/2012 | Kamath et al. |
| 8,251,906 B2 | 8/2012 | Brauker et al. |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,257,259 B2 | 9/2012 | Brauker et al. |
| 8,260,393 B2 | 9/2012 | Kamath et al. |
| 8,265,725 B2 | 9/2012 | Brauker et al. |
| 8,275,437 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,282,550 B2 | 10/2012 | Rasdal et al. |
| 8,285,354 B2 | 10/2012 | Goode et al. |
| 8,287,453 B2 | 10/2012 | Li et al. |
| 8,290,559 B2 | 10/2012 | Shariati et al. |
| 8,290,560 B2 | 10/2012 | Kamath et al. |
| 8,290,561 B2 | 10/2012 | Brauker et al. |
| 8,290,562 B2 | 10/2012 | Goode, Jr. et al. |
| 8,292,810 B2 | 10/2012 | Goode, Jr. et al. |
| 8,298,142 B2 | 10/2012 | Simpson et al. |
| 8,311,749 B2 | 11/2012 | Brauker et al. |
| 8,313,434 B2 | 11/2012 | Brister et al. |

(56) References Cited

U.S. PATENT DOCUMENTS

| | | |
|---|---|---|
| 8,321,149 B2 | 11/2012 | Brauker et al. |
| 8,332,008 B2 | 12/2012 | Goode et al. |
| 8,346,338 B2 | 1/2013 | Goode, Jr. et al. |
| 8,364,229 B2 | 1/2013 | Simpson et al. |
| 8,369,919 B2 | 2/2013 | Kamath et al. |
| 8,374,667 B2 | 2/2013 | Brauker et al. |
| 8,386,004 B2 | 2/2013 | Kamath et al. |
| 8,394,021 B2 | 3/2013 | Goode et al. |
| 9,737,250 B2 | 8/2017 | Hughes et al. |
| 9,788,765 B2 | 10/2017 | Boock et al. |
| 9,974,472 B2 | 5/2018 | Hayter et al. |
| 10,598,627 B2 | 3/2020 | Estes et al. |
| 2003/0032874 A1 | 2/2003 | Rhodes et al. |
| 2005/0033132 A1 | 2/2005 | Shults et al. |
| 2005/0051427 A1 | 3/2005 | Brauker et al. |
| 2005/0056552 A1 | 3/2005 | Simpson et al. |
| 2005/0090607 A1 | 4/2005 | Tapsak et al. |
| 2005/0143635 A1 | 6/2005 | Kamath et al. |
| 2005/0176136 A1 | 8/2005 | Burd et al. |
| 2005/0182451 A1 | 8/2005 | Griffin et al. |
| 2005/0245799 A1 | 11/2005 | Brauker et al. |
| 2006/0015020 A1 | 1/2006 | Neale et al. |
| 2006/0016700 A1 | 1/2006 | Brister et al. |
| 2006/0020188 A1 | 1/2006 | Kamath et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036140 A1 | 2/2006 | Brister et al. |
| 2006/0036143 A1 | 2/2006 | Brister et al. |
| 2006/0040402 A1 | 2/2006 | Brauker et al. |
| 2006/0068208 A1 | 3/2006 | Tapsak et al. |
| 2006/0142651 A1 | 6/2006 | Brister et al. |
| 2006/0155180 A1 | 7/2006 | Brister et al. |
| 2006/0195029 A1 | 8/2006 | Shults et al. |
| 2006/0198864 A1 | 9/2006 | Shults et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0224108 A1 | 10/2006 | Brauker et al. |
| 2006/0235285 A1 | 10/2006 | Brister et al. |
| 2006/0249381 A1 | 11/2006 | Petisce et al. |
| 2006/0252027 A1 | 11/2006 | Petisce et al. |
| 2006/0253012 A1 | 11/2006 | Petisce et al. |
| 2006/0257995 A1 | 11/2006 | Simpson et al. |
| 2006/0258761 A1 | 11/2006 | Boock et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2007/0027370 A1 | 2/2007 | Brauker et al. |
| 2007/0032706 A1 | 2/2007 | Kamath et al. |
| 2007/0032718 A1 | 2/2007 | Shults et al. |
| 2007/0045902 A1 | 3/2007 | Brauker et al. |
| 2007/0059196 A1 | 3/2007 | Brister et al. |
| 2007/0066873 A1 | 3/2007 | Kamath et al. |
| 2007/0173709 A1 | 7/2007 | Petisce et al. |
| 2007/0173710 A1 | 7/2007 | Petisce et al. |
| 2007/0208245 A1 | 9/2007 | Brauker et al. |
| 2007/0208246 A1 | 9/2007 | Brauker et al. |
| 2007/0232879 A1 | 10/2007 | Brister et al. |
| 2007/0235331 A1 | 10/2007 | Simpson et al. |
| 2007/0299617 A1 | 12/2007 | Willis |
| 2008/0000079 A1 | 1/2008 | Gabriel et al. |
| 2008/0000779 A1 | 1/2008 | Wang et al. |
| 2008/0027287 A1 | 1/2008 | Shah et al. |
| 2008/0045824 A1 | 2/2008 | Tapsak et al. |
| 2008/0076974 A1 | 3/2008 | Yamazaki et al. |
| 2008/0083617 A1 | 4/2008 | Simpson et al. |
| 2008/0086044 A1 | 4/2008 | Brister et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0161664 A1 | 7/2008 | Mastrototaro et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194938 A1 | 8/2008 | Brister et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0214915 A1 | 9/2008 | Brister et al. |
| 2008/0228054 A1 | 9/2008 | Shults et al. |
| 2008/0242961 A1 | 10/2008 | Brister et al. |
| 2008/0249385 A1* | 10/2008 | Phan ............... A61B 5/14532 600/347 |
| 2008/0262469 A1 | 10/2008 | Brister et al. |
| 2008/0275313 A1 | 11/2008 | Brister et al. |
| 2008/0287762 A1 | 11/2008 | Hayter et al. |
| 2008/0287765 A1 | 11/2008 | Rasdal et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0018424 A1 | 1/2009 | Kamath et al. |
| 2009/0023222 A1 | 1/2009 | Wu et al. |
| 2009/0030294 A1 | 1/2009 | Petisce et al. |
| 2009/0030641 A1 | 1/2009 | Fjield et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043288 A1 | 2/2009 | Petrakis |
| 2009/0043525 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076360 A1 | 3/2009 | Brister et al. |
| 2009/0082693 A1 | 3/2009 | Stafford |
| 2009/0099436 A1 | 4/2009 | Brister et al. |
| 2009/0105605 A1 | 4/2009 | Abreu |
| 2009/0120810 A1 | 5/2009 | Phan et al. |
| 2009/0124877 A1 | 5/2009 | Goode, Jr. et al. |
| 2009/0124879 A1 | 5/2009 | Brister et al. |
| 2009/0124964 A1 | 5/2009 | Leach et al. |
| 2009/0131769 A1 | 5/2009 | Leach et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0163790 A1 | 6/2009 | Brister et al. |
| 2009/0178459 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192751 A1 | 7/2009 | Kamath et al. |
| 2009/0203981 A1 | 8/2009 | Brauker et al. |
| 2009/0216103 A1 | 8/2009 | Brister et al. |
| 2009/0240120 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0275815 A1 | 11/2009 | Bickoff et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0020341 A1 | 1/2010 | Enjuji |
| 2010/0030484 A1 | 2/2010 | Brauker et al. |
| 2010/0036215 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |

(56) References Cited

U.S. PATENT DOCUMENTS

| | | |
|---|---|---|
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0087900 A1 | 4/2010 | Flint |
| 2010/0096259 A1 | 4/2010 | Zhang et al. |
| 2010/0121169 A1 | 5/2010 | Petisce et al. |
| 2010/0161269 A1 | 6/2010 | Kamath et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185075 A1 | 7/2010 | Brister et al. |
| 2010/0191082 A1 | 7/2010 | Brister et al. |
| 2010/0198035 A1 | 8/2010 | Kamath et al. |
| 2010/0198036 A1 | 8/2010 | Kamath et al. |
| 2010/0212583 A1 | 8/2010 | Brister et al. |
| 2010/0217557 A1 | 8/2010 | Kamath et al. |
| 2010/0219085 A1 | 9/2010 | Oviatt, Jr. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0230285 A1 | 9/2010 | Hoss et al. |
| 2010/0240975 A1 | 9/2010 | Goode, Jr. et al. |
| 2010/0240976 A1 | 9/2010 | Goode, Jr. et al. |
| 2010/0261987 A1 | 10/2010 | Kamath et al. |
| 2010/0268304 A1 | 10/2010 | Matos |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0292557 A1 | 11/2010 | Pesach et al. |
| 2010/0298684 A1 | 11/2010 | Leach et al. |
| 2010/0319436 A1 | 12/2010 | Sun et al. |
| 2010/0324403 A1 | 12/2010 | Brister et al. |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021932 A1 | 1/2011 | Kim et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0077490 A1 | 3/2011 | Simpson et al. |
| 2011/0118579 A1 | 5/2011 | Goode, Jr. et al. |
| 2011/0124992 A1 | 5/2011 | Brauker et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0144465 A1 | 6/2011 | Shults et al. |
| 2011/0178378 A1 | 7/2011 | Brister et al. |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0218489 A1 | 9/2011 | Mastrototaro et al. |
| 2011/0224516 A1 | 9/2011 | Romey et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0237916 A1 | 9/2011 | Hanson et al. |
| 2011/0253533 A1 | 10/2011 | Shults et al. |
| 2011/0263958 A1 | 10/2011 | Brauker et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0290645 A1 | 12/2011 | Brister et al. |
| 2011/0313543 A1 | 12/2011 | Brauker et al. |
| 2011/0320130 A1 | 12/2011 | Valdes et al. |
| 2012/0028283 A1 | 2/2012 | Hoss et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0097554 A1 | 4/2012 | Shah et al. |
| 2012/0108934 A1 | 5/2012 | Valdes et al. |
| 2012/0130214 A1 | 5/2012 | Brister et al. |
| 2012/0172691 A1 | 7/2012 | Brauker et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0203467 A1 | 8/2012 | Kamath et al. |
| 2012/0209098 A1 | 8/2012 | Goode, Jr. et al. |
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215461 A1 | 8/2012 | Goode, Jr. et al. |
| 2012/0215462 A1 | 8/2012 | Goode, Jr. et al. |
| 2012/0215496 A1 | 8/2012 | Kamath et al. |
| 2012/0220979 A1 | 8/2012 | Brauker et al. |
| 2012/0226121 A1 | 9/2012 | Kamath et al. |
| 2012/0228134 A1 | 9/2012 | Simpson et al. |
| 2012/0238852 A1 | 9/2012 | Brauker et al. |
| 2012/0245448 A1 | 9/2012 | Shariati et al. |
| 2012/0245855 A1 | 9/2012 | Kamath et al. |
| 2012/0255875 A1 | 10/2012 | Vicente et al. |
| 2012/0258748 A1 | 10/2012 | San Vicente et al. |
| 2012/0259191 A1 | 10/2012 | Shariati et al. |
| 2012/0260323 A1 | 10/2012 | San Vicente et al. |
| 2012/0262298 A1 | 10/2012 | Bohm et al. |
| 2012/0265035 A1 | 10/2012 | Bohm et al. |
| 2012/0265036 A1 | 10/2012 | Estes et al. |
| 2012/0265037 A1 | 10/2012 | Bohm et al. |
| 2012/0277562 A1 | 11/2012 | Brister et al. |
| 2012/0277566 A1 | 11/2012 | Kamath et al. |
| 2012/0283541 A1 | 11/2012 | Kamath et al. |
| 2012/0283543 A1 | 11/2012 | Brauker et al. |
| 2012/0296311 A1 | 11/2012 | Brauker et al. |
| 2012/0302854 A1 | 11/2012 | Kamath et al. |
| 2012/0302855 A1 | 11/2012 | Kamath et al. |
| 2012/0323100 A1 | 12/2012 | Kamath et al. |
| 2013/0012798 A1 | 1/2013 | Brister et al. |
| 2013/0030273 A1 | 1/2013 | Tapsak et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0053665 A1 | 2/2013 | Hughes et al. |
| 2013/0053666 A1 | 2/2013 | Hughes et al. |
| 2013/0060105 A1 | 3/2013 | Shah et al. |
| 2013/0112573 A1 | 5/2013 | Noble et al. |
| 2013/0331673 A1 | 12/2013 | Gautham et al. |
| 2014/0005505 A1 | 1/2014 | Peyser et al. |
| 2014/0005508 A1 | 1/2014 | Estes et al. |

(56) References Cited

U.S. PATENT DOCUMENTS

| | | |
|---|---|---|
| 2014/0005509 A1 | 1/2014 | Bhavaraju et al. |
| 2015/0090589 A1 | 4/2015 | Estes et al. |
| 2020/0281511 A1 | 9/2020 | Bhavaraju et al. |

OTHER PUBLICATIONS

International Preliminary Report on Patentability for Application No. PCT/US2013/047527 dated Jan. 8, 2015, 12 pages.

International Preliminary Report on Patentability for Application No. PCT/US2013/047537 dated Jan. 8, 2015, 8 pages.

International Preliminary Report on Patentability for Application No. PCT/US2013/047543 dated Jan. 8, 2015, 12 pages.

International Search Report and Written Opinion for Application No. PCT/US2013/047527 dated Nov. 15, 2013, 17 pages.

International Search Report and Written Opinion for Application No. PCT/US2013/047537 dated Sep. 9, 2013, 11 pages.

International Search Report and Written Opinion for Application No. PCT/US2013/047543 dated Nov. 15, 2013, 16 pages.

Klueh U., et al., "Metabolic Biofouling of Glucose Sensors in Vivo: Role of Tissue Microhemorrhages," J Diabetes Science Technol, May 2011, vol. 5 (3), pp. 583-595.

Office Action for European Application No. 13735149.0, dated Nov. 2, 2020, 4 pages.

Office Action for European Application No. 13742300.0, dated Nov. 2, 2020, 4 pages.

Office Action from European Patent Application No. 13735148.2, dated Nov. 11, 2020, 7 pages.

US 8,027,708, 11/1999, Shults et al. (withdrawn)

Communication Under Rule No. 71(3) for EP Application No. 13735149.0, dated Jun. 23, 2021, 103 pages.

Office Action for European Application No. 13742300.0, dated Apr. 26, 2021, 2 pages.

* cited by examiner

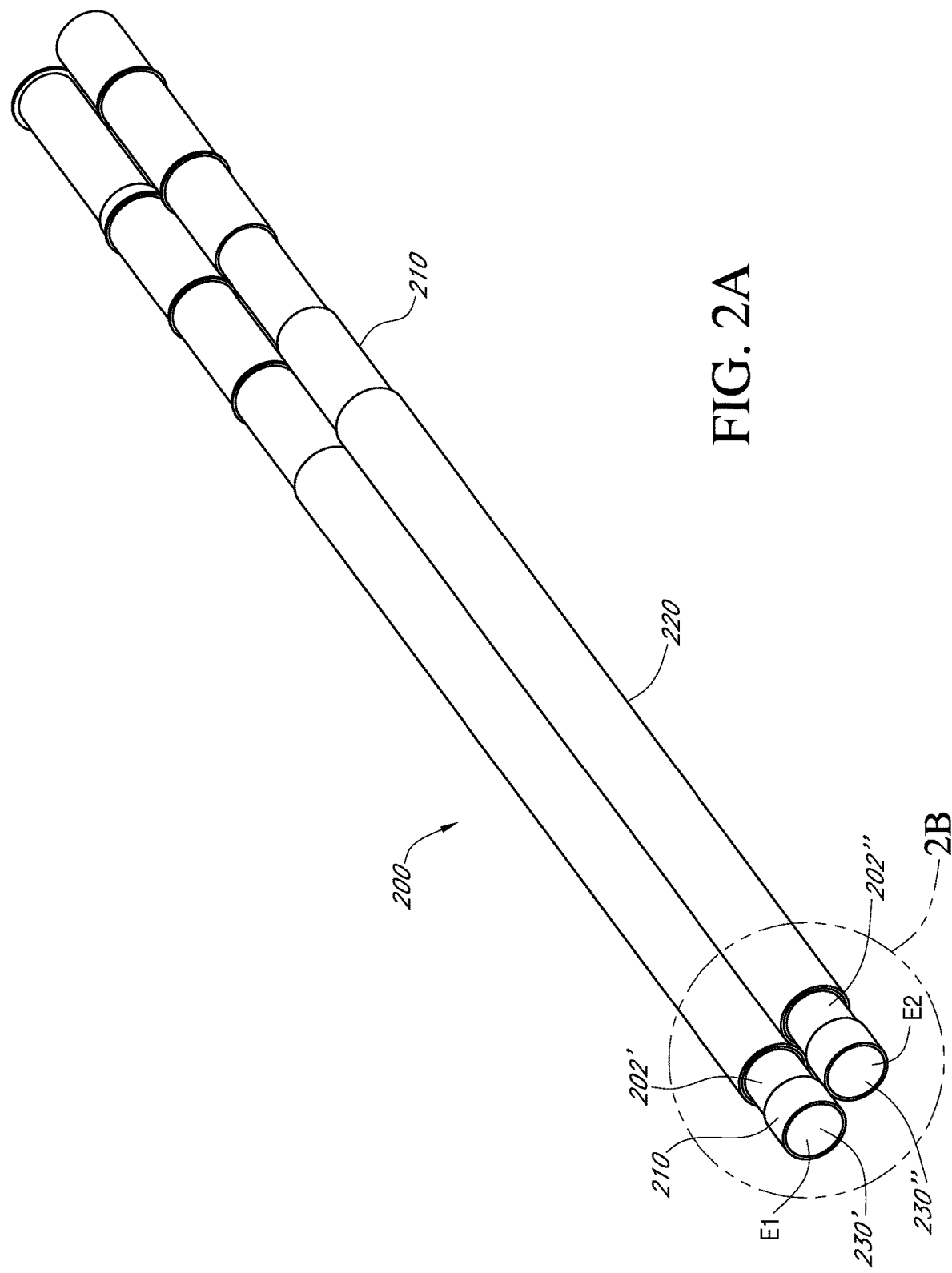

DEVICES, SYSTEMS, AND METHODS TO COMPENSATE FOR EFFECTS OF TEMPERATURE ON IMPLANTABLE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 14/567,293, filed Dec. 11, 2014, which is a continuation of U.S. application Ser. No. 13/747,746, filed Jan. 23, 2013, which claims the benefit of U.S. Provisional Application No. 61/666,618, filed Jun. 29, 2012. Each of the aforementioned applications is incorporated by reference herein in its entirety, and each is hereby expressly made a part of this specification.

FIELD OF THE INVENTION

The embodiments described herein relate generally to devices, systems, and methods for determining a temperature compensation factor based on a temperature of a sensor.

BACKGROUND OF THE INVENTION

Diabetes mellitus is a chronic disease which occurs when the pancreas does not produce enough insulin (Type I), or when the body cannot effectively use the insulin it produces (Type II). This condition typically leads to an increased concentration of glucose in the blood (hyperglycemia), which can cause an array of physiological derangements (such as, for example, kidney failure, skin ulcers, or bleeding into the vitreous of the eye) associated with the deterioration of small blood vessels. Sometimes, a hypoglycemic reaction (low blood sugar) is induced by an inadvertent overdose of insulin, or after a normal dose of insulin or glucose-lowering agent accompanied by extraordinary exercise or insufficient food intake.

Electrochemical sensors are useful in chemistry and medicine to determine the presence or concentration of a biological analyte. Such sensors are useful, for example, to monitor glucose in diabetic patients and lactate during critical care events. A variety of intravascular, transcutaneous and implantable sensors have been developed for continuously detecting and quantifying blood glucose values. Many conventional implantable glucose sensors suffer from complications within the body and provide only short-term or less-than-accurate sensing of blood glucose. Additionally, many conventional transcutaneous sensors have problems in accurately sensing and reporting back glucose or analyte values continuously over extended periods of time due to non-analyte-related signals caused by interfering species or unknown noise-causing events.

Measuring temperature in a sensor environment can be an important aspect of ensuring accurate detection and measurement of analytes for a variety of reasons. For example, changes in temperature are noted as having a corresponding effect on changes in sensor sensitivity. This relationship may be based on a number of factors, including, for example, a change in membrane permeability, or a change in enzyme activity.

Temperature considerations are also important in determining accurate analyte measurements due to the fact that the temperature at which a particular sensor may have been calibrated may be different than the temperature of the sensor's operational environment. Further, because sensor sensitivity changes as temperature changes, it is important to measure the temperature of the sensor environment at or substantially near the time of analyte measurement because the sensor sensitivity may be different than at the time of sensor calibration.

Electrochemical analyte sensors are sensitive to temperature changes because such changes affect enzymatic reaction kinetics. In most patients, homeostatic mechanisms maintain body temperatures within a fairly constant range. Heretofore, the calibration process, wherein a sensor is calibrated at a given temperature, has been relied upon to provide adequate compensation for temperature effects. While reliance on the calibration process may be adequate for sensors placed in areas of tissue that are exposed to relatively small fluctuations in body temperature (such as, for example, subcutaneous adipose tissue in, for example, the abdomen), sensors placed in alternate sites, however, (such as, for example, the dorsal upper arm) may be exposed to greater temperature variations. Similarly, sensor performance may be altered (namely, due to changes in sensor properties, such as sensor sensitivity) when patients are febrile or exposed to large fluctuations in ambient temperatures.

SUMMARY OF THE INVENTION

A method for real-time or dynamic temperature compensation is desirable to account for changes in temperature in order to ensure accuracy in continuous analyte sensing. Real time temperature information (e.g., an actual temperature, a relative difference in temperature, or a change in temperature, or a measurement of some property characteristic of an actual temperature, a relative difference in temperature, or a change in temperature) indicative of in vivo conditions ambient to the continuous glucose sensor can be obtained by various methods, as herein described. Upon securing temperature information, a processor or other electronics circuitry can employ the temperature information to generate a correction factor, which can then be employed to correct an analyte measurement obtained by the continuous glucose sensor.

Accordingly, in a first aspect a device is provided for continuous in vivo measurement of glucose concentrations in a host, comprising: at least one electrode operatively connected to electronic circuitry configured to generate a signal representative of a concentration of glucose in a host; at least one membrane located over at least a portion of the electrode, the at least one membrane comprising an enzyme configured to catalyze a reaction of glucose and oxygen from a biological fluid in contact with the membrane in vivo; and a temperature sensor configured to measure at least one of an in vivo temperature or a change in temperature in vivo.

In an embodiment of the first aspect, the at least one electrode comprises a first electrode and a second electrode.

In an embodiment of the first aspect, the at least one membrane comprises a first membrane located over at least a portion of the first electrode and a second membrane located over at least a portion of the second electrode, and wherein the first membrane and the second membrane each have a different temperature coefficient.

In an embodiment of the first aspect, the first membrane and the second membrane each have a different composition.

In an embodiment of the first aspect, the first membrane and the second membrane are each configured to exhibit a different change in dimension in response to a change in temperature in vivo.

In an embodiment of the first aspect, the first membrane and the second membrane are each configured to exhibit a different change in electrical conductivity in response to a change in temperature in vivo.

In an embodiment of the first aspect, the device further comprises sensor electronics configured to apply at least one potential to at least one of the first electrode or the second electrode.

In an embodiment of the first aspect, the at least one potential includes a first potential that is applied to the first electrode and a second potential that is applied to the second electrode.

In an embodiment of the first aspect, the first potential is different from the second potential.

In an embodiment of the first aspect, the device further comprises a connector configured to connect the first electrode and the second electrode, wherein the connector comprises a thermistor.

In an embodiment of the first aspect, the connector further comprises a diode.

In an embodiment of the first aspect, the connector further comprises a capacitor.

In an embodiment of the first aspect, the device further comprises a third electrode, wherein the first electrode and the second electrode are each working electrodes and the third electrode is a reference electrode.

In an embodiment of the first aspect, the device further comprises a connector configured to connect the first electrode, the second electrode, and the third electrode, wherein the connector comprises a thermistor and a transistor.

In an embodiment of the first aspect, the temperature sensor is configured to measure a stimulus signal passed across the first electrode and the second electrode.

In an embodiment of the first aspect, the stimulus signal is an impedance measurement.

In an embodiment of the first aspect, the device further comprises a first reference electrode or a first counter electrode, and a second reference electrode or a second counter electrode, wherein the temperature sensor is configured to measure a stimulus signal passed between the first electrode and the second electrode.

In an embodiment of the first aspect, the device is configured to apply a first bias potential to the first electrode and a second bias potential to the second electrode, wherein the second bias potential varies over time, and wherein the temperature sensor is configured to measure a change in a property of the device in response to a change in the second bias potential.

In an embodiment of the first aspect, the temperature sensor is configured to measure a change in sensitivity to glucose in response to a change in temperature in vivo.

In an embodiment of the first aspect, the at least one electrode comprises a thermally conductive core, and wherein the temperature sensor is configured to measure a change in temperature of the thermally conductive core.

In an embodiment of the first aspect, the at least one electrode comprises a portion comprising a shape memory material, and wherein the temperature sensor is configured to measure a pressure change of the shape memory material responsive to a temperature change in vivo.

In an embodiment of the first aspect, the temperature sensor comprises a fiber optic sensor configured to measure a temperature in vivo, and wherein the fiber optic sensor is embedded within the electrode or affixed to the electrode.

In an embodiment of the first aspect, the device comprises a processor configured to use a priori sensitivity information.

In a second aspect, a method is provided for processing data from a continuous glucose sensor, the method comprising: receiving sensor data from a continuous glucose sensor, the sensor data comprising at least one sensor data point corresponding to a first time period, wherein the at least one sensor data point is representative of a glucose concentration in a host for the first time period; determining, using a temperature sensor, a temperature of the continuous glucose sensor; and processing, using sensor electronics, the at least one sensor data point responsive to the temperature of the continuous glucose sensor.

In an embodiment of the second aspect, determining a temperature comprises measuring a temperature.

In an embodiment of the second aspect, determining a temperature comprises measuring a change in temperature.

In an embodiment of the second aspect, processing, using sensor electronics, the at least one sensor data point comprises adjusting the sensor data for the first time period to compensate for an effect of the temperature on the continuous glucose sensor.

In an embodiment of the second aspect, the method further comprises: receiving, from an in vitro reference glucose sensor, a reference data point corresponding to a second time period; wherein processing, using sensor electronics, the at least one sensor data point comprises adjusting the sensor data to compensate for a change in temperature between the first time period and the second time period.

In an embodiment of the second aspect, processing, using sensor electronics, the at least one sensor data point comprises: determining a sensitivity value of the continuous glucose sensor; forming a conversion function based at least in part on the sensitivity value; and determining a glucose output value by applying the conversion function to the at least one sensor data point.

In an embodiment of the second aspect, the method further comprises adjusting the sensitivity value responsive to the determined temperature.

In an embodiment of the second aspect, determining the sensitivity value is performed by applying a priori sensitivity information comprising sensor sensitivity information as a function of temperature.

In an embodiment of the second aspect, the a priori sensitivity information is stored in the sensor selectronics prior to use of the continuous glucose sensor.

In a third aspect, a method is provided for processing data from a continuous glucose sensor, the method comprising: determining a first sensitivity of a continuous glucose sensor at a first temperature; receiving, from the continuous glucose sensor, sensor data, the sensor data comprising at least one sensor data point corresponding to a first time period, wherein the at least one sensor data point is representative of a glucose concentration of a host for the first time period; determining, using a temperature sensor, a second temperature of the continuous glucose sensor; determining a second sensitivity of the continuous glucose sensor by adjusting the first sensitivity to compensate for a difference between the first temperature and the second temperature; and processing, using sensor electronics, the at least one sensor data point responsive to the determination of the second sensitivity.

In an embodiment of the third aspect, determining the second sensitivity is performed by applying a priori sensitivity information comprising sensor sensitivity information as a function of temperature.

In an embodiment of the third aspect, the a priori sensitivity information is stored in the sensor electronics prior to use of the continuous glucose sensor.

In an embodiment of the third aspect, the a priori sensitivity information comprises a relationship between a temperature coefficient and the first sensitivity.

In an embodiment of the third aspect, determining the second sensitivity comprises: determining a temperature coefficient; and determining the second sensitivity as a function of the determined temperature coefficient.

In an embodiment of the third aspect, the method further comprises updating, over time, the relationship between the temperature coefficient and the first sensitivity.

In an embodiment of the third aspect, the method further comprises: determining, using the temperature sensor, a third temperature of the continuous glucose sensor; determining a third sensitivity of the continuous glucose sensor by adjusting at least one of the first sensitivity or the second sensitivity to compensate for a difference between the third temperature and at least one of the first temperature or the second temperature; and processing, using sensor electronics, the sensor data responsive to the determination of the third sensitivity.

Any embodiment of the first aspect may be employed in combination with any one or more of the other embodiments of the first aspect. Any embodiment of the second aspect may be employed in combination with any one or more of the other embodiments of the second aspect. Any embodiment of the third aspect may be employed in combination with any one or more of the other embodiments of the third aspect. Likewise, any one or more of the methods of the second and/or third aspects and/or their associated embodiments may be employed with the device of the first aspect or any one or more associated embodiments of the first aspect.

BRIEF DESCRIPTION OF THE DRAWINGS

These and other features and advantages will be appreciated, as they become better understood by reference to the following detailed description when considered in connection with the accompanying drawings, wherein:

FIG. 2A is a perspective-view schematic illustrating an in vivo portion of a multi-electrode analyte sensor, in another embodiment.

DETAILED DESCRIPTION OF THE PREFERRED EMBODIMENT

Definitions

Figure 1:
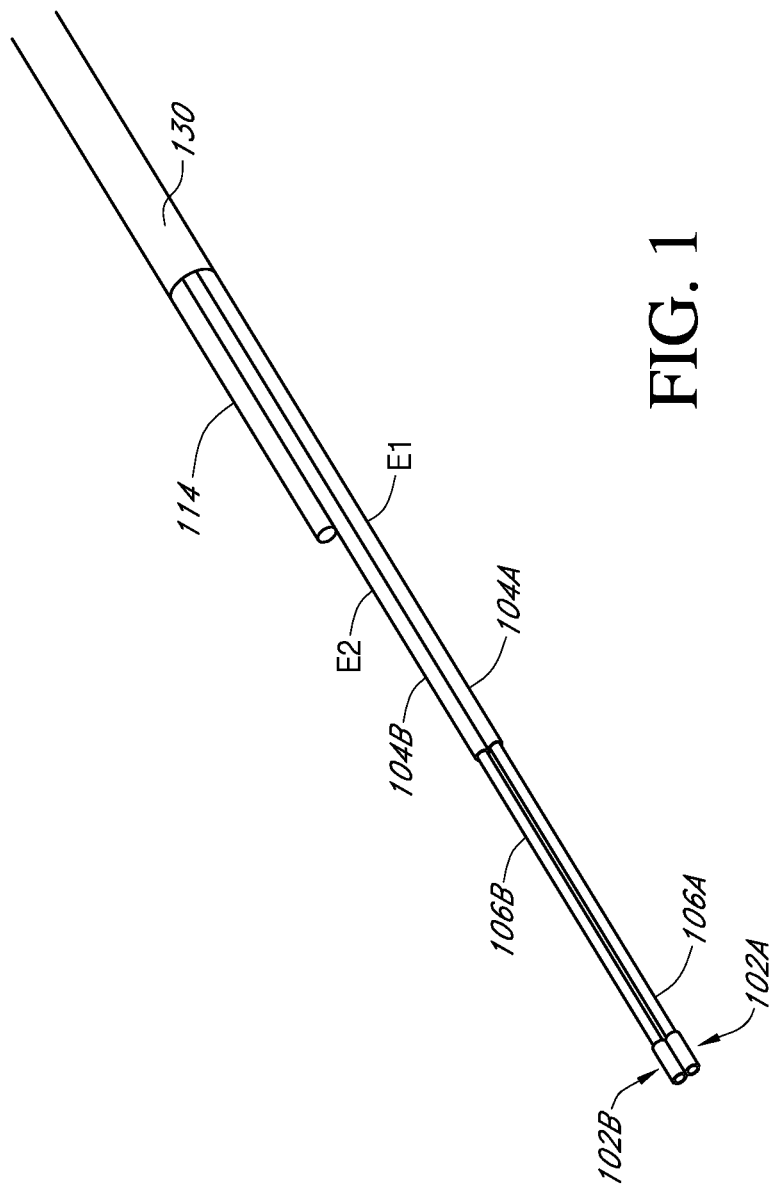
FIG. 1 is a perspective-view schematic illustrating an in vivo portion of a multi-electrode analyte sensor, in one embodiment.

In order to facilitate an understanding of the embodiments described herein, a number of terms are defined below.

The term "about," as used herein, is a broad term, and is to be given its ordinary and customary meaning to a person of ordinary skill in the art (and is not to be limited to a special or customized meaning), and when associated with any numerical values or ranges, refers without limitation to the understanding that the amount or condition the terms modify can vary some beyond the stated amount so long as the function of the embodiment is realized.

The term "A/D Converter," as used herein, is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The term "analyte," as used herein, is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethyl chloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A, S, C, E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "baseline," as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal. In certain embodiments, the value of b (i.e., the baseline) can be zero or about zero. This can be the result of a baseline-subtracting electrode or low bias potential settings, for example. As a result, for these embodiments, calibration can be defined by solving for the equation y=mx.

The term "biological sample," as used herein, is a broad term, and is to be given its ordinary and customary meaning to a person of ordinary skill in the art (and is not to be limited to a special or customized meaning), and refers without limitation to sample derived from the body or tissue of a host, such as, for example, blood, interstitial fluid, spinal fluid, saliva, urine, tears, sweat, or other like fluids.

The term "calibration," as used herein, is a broad term, and is to be given its ordinary and customary meaning to a person of ordinary skill in the art (and is not to be limited to a special or customized meaning), and refers without limitation to the process of determining the graduation of a sensor giving quantitative measurements (e.g., analyte concentration). As an example, calibration may be updated or recalibrated over time to account for changes associated with the sensor, such as changes in sensor sensitivity and sensor background. In addition, calibration of the sensor can involve, automatic, self-calibration, that is, calibration without using reference analyte values after point of use.

The term "co-analyte," as used herein, is a broad term, and is to be given its ordinary and customary meaning to a person of ordinary skill in the art (and it is not to be limited to a special or customized meaning), and refers without limitation to a molecule required in an enzymatic reaction to react with the analyte and the enzyme to form the specific product being measured. In one embodiment of a glucose sensor, an enzyme, glucose oxidase (GOX) is provided to react with glucose and oxygen (the co-analyte) to form hydrogen peroxide.

The term "comprising," as used herein, is synonymous with "including," "containing," or "characterized by," and is inclusive or open-ended and does not exclude additional, unrecited elements or method steps.

The term "computer," as used herein, is a broad term, and is to be given its ordinary and customary meaning to a person of ordinary skill in the art (and it is not to be limited to a special or customized meaning), and refers without limitation to machine that can be programmed to manipulate data.

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (such as, for example, by continuously or continually adjusting or determining the sensor's sensitivity and background), for example, at time intervals ranging from fractions of a second up to, for example, 1, 2, or 5 minutes, or longer.

The phrase "continuous glucose sensing," as used herein, is a broad term, and is to be given its ordinary and customary meaning to a person of ordinary skill in the art (and it is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "dielectric strength," as used herein, is a broad term, and is to be given its ordinary and customary meaning to a person of ordinary skill in the art (and is not to be limited to a special or customized meaning), and refers without limitation to the maximum electrical field strength that a material can withstand intrinsically without breaking down, that is, without experiencing failure of the material's insulating properties, and, more generally, is an intrinsic property of the bulk material being dependent on the configuration of the material or the electrodes with which the field is applied, as measured in MV/m.

The term "distal," as used herein, is a broad term, and is to be given its ordinary and customary meaning to a person of ordinary skill in the art (and it is not to be limited to a special or customized meaning), and refers without limitation to spaces relatively far from a point of reference, such as an origin or a point of attachment.

The term "domain," as used herein, is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

The term "electrical conductor," as used herein, is a broad term, and is to be given its ordinary and customary meaning to a person of ordinary skill in the art (and is not to be limited to a special or customized meaning) and refers without limitation to materials that contain movable charges of electricity. When an electric potential difference is impressed across separate points on a conductor, the mobile charges within the conductor are forced to move, and an electric current between those points appears in accordance with Ohm's law.

The term "electrical conductance," as used herein, is a broad term, and is to be given its ordinary and customary meaning to a person of ordinary skill in the art (and is not to be limited to a special or customized meaning) and refers without limitation to the propensity of a material to behave as an electrical conductor. In some embodiments, the term refers to a sufficient amount of electrical conductance (e.g., material property) to provide a necessary function (electrical conduction).

The terms "electrochemically reactive surface" and "electroactive surface," as used herein, are broad terms, and are to be given their ordinary and customary meaning to a person of ordinary skill in the art (and they are not to be limited to a special or customized meaning), and refer without limitation to the surface of an electrode where an electrochemical reaction takes place. In one embodiment, a working electrode measures hydrogen peroxide ($H_2O_2$) creating a measurable electronic current.

The term "electrode," as used herein, is a broad term, and is to be given its ordinary and customary meaning to a person of ordinary skill in the art (and it is not to be limited to a special or customized meaning), and refers without limitation to a conductor through which electricity enters or leaves something such as a battery or a piece of electrical equipment. In one embodiment, the electrodes are the metallic portions of a sensor (e.g., electrochemically reactive surfaces) that are exposed to the extracellular milieu, for detecting the analyte. In some embodiments, the term electrode includes the conductive wires or traces that electrically connect the electrochemically reactive surface to connectors (for connecting the sensor to electronics) or to the electronics.

The term "elongated conductive body," as used herein, is a broad term and is to be given its ordinary and customary meaning to a person of ordinary skill in the art (and it is not to be limited to a special or customized meaning), and refers without limitation to an elongated body formed at least in part of a conductive material and includes any number of coatings that may be formed thereon. By way of example, an "elongated conductive body" may mean a bare elongated conductive core (e.g., a metal wire) or an elongated conductive core coated with one, two, three, four, five, or more than five layers of material, each of which may or may not be conductive.

The term "enzyme," as used herein, is a broad term, and is to be given its ordinary and customary meaning to a person of ordinary skill in the art (and it is not to be limited to a special or customized meaning), and refers without limitation to a protein or protein-based molecule that speeds up a chemical reaction occurring in a living thing. Enzymes may act as catalysts for a single reaction, converting a reactant (also called an analyte herein) into a specific product. In one embodiment of a glucose oxidase-based glucose sensor, an enzyme, glucose oxidase (GOX) is provided to react with glucose (the analyte) and oxygen to form hydrogen peroxide.

The term "filtering," as used herein, is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "function," as used herein, is a broad term, and is to be given its ordinary and customary meaning to a person of ordinary skill in the art (and it is not to be limited to a special or customized meaning), and refers without limitation to an action or use for which something is suited or designed.

The term "GOx," as used herein, is a broad term, and is to be given its ordinary and customary meaning to a person of ordinary skill in the art (and is not to be limited to a special or customized meaning), and refers without limitation to the enzyme Glucose Oxidase (e.g., GOx is an abbreviation).

The term "helix," as used herein, is a broad term, and is to be given its ordinary and customary meaning to a person of ordinary skill in the art (and is not to be limited to a special or customized meaning), and refers without limitation to a spiral or coil, or something in the form of a spiral or coil (such as, for example, a corkscrew or a coiled spring). In one example, a helix is a mathematical curve that lies on a cylinder or cone and makes a constant angle with the straight lines lying in the cylinder or cone. A "double helix" is a pair of parallel helices intertwined about a common axis, such as but not limited to that in the structure of DNA.

The term "host," as used herein, is a broad term, and is to be given its ordinary and customary meaning to a person of ordinary skill in the art (and is not to be limited to a special or customized meaning), and refers without limitation to animals, including humans.

The term "inactive enzyme," as used herein, is a broad term, and is to be given its ordinary and customary meaning to a person of ordinary skill in the art (and is not to be limited to a special or customized meaning), and refers without limitation to an enzyme (such as, for example, glucose oxidase, GOx) that has been rendered inactive (e.g., by denaturing of the enzyme) and has substantially no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The terms "insulative properties," "electrical insulator," and "insulator," as used herein, are broad terms, and are to be given their ordinary and customary meaning to a person of ordinary skill in the art (and are not to be limited to a special or customized meaning) and refer without limitation to the tendency of materials that lack mobile charges to prevent movement of electrical charges between two points. In one embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The terms "interferent" and "interfering species," as used herein, are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured, producing a false positive signal.

The term "in vivo portion," as used herein, is a broad term, and is to be given its ordinary and customary meaning to a person of ordinary skill in the art (and is not to be limited to a special or customized meaning), and refers without limitation to a portion of a device that is to be implanted or inserted into the host. In one embodiment, an in vivo portion of a transcutaneous sensor is a portion of the sensor that is inserted through the host's skin and resides within the host.

The term "membrane system," as used herein, is a broad term, and is to be given its ordinary and customary meaning to a person of ordinary skill in the art (and is not to be limited to a special or customized meaning), and refers without limitation to a permeable or semi-permeable membrane that can include two or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "operably connected," as used herein, is a broad term, and is to be given its ordinary and customary meaning to a person of ordinary skill in the art (and is not to be limited to a special or customized meaning), and refers without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "potentiostat," as used herein, is a broad term, and is to be given its ordinary and customary meaning to a person of ordinary skill in the art (and is not to be limited to a special or customized meaning), and refers without limitation to an electrical system that applies a potential between the working and reference electrodes of a two- or three-electrode cell at a preset value and measures the current flow through the working electrode. The potentiostat forces whatever current is necessary to flow between the working and counter electrodes to keep the desired potential, as long as the needed cell voltage and current do not exceed the compliance limits of the potentiostat.

The terms "processor module" and "microprocessor," as used herein, are broad terms, and are to be given their ordinary and customary meaning to a person of ordinary skill in the art (and they are not to be limited to a special or customized meaning), and refer without limitation to a computer system, state machine, processor, or the like designed to perform arithmetic and logic operations using logic circuitry that responds to and processes the basic instructions that drive a computer.

The term "proximal," as used herein, is a broad term, and is to be given its ordinary and customary meaning to a person of ordinary skill in the art (and it is not to be limited to a special or customized meaning), and refers without limitation to near to a point of reference such as an origin or a point of attachment.

The terms "raw data stream" and "data stream," as used herein, are broad terms, and are to be given their ordinary and customary meaning to a person of ordinary skill in the art (and they are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "RAM," as used herein, is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "ROM," as used herein, is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The terms "reference analyte values" and "reference data," as used herein, are broad terms, and are to be given their ordinary and customary meaning to a person of ordinary skill in the art (and they are not to be limited to a special or customized meaning), and refer without limitation to reference data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or a YSI (Yellow Springs Instruments) test, for example.

The term "regression," as used herein, is a broad term, and is to be given its ordinary and customary meaning to a person of ordinary skill in the art (and it is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electroactive surface at one location on the body and an electronic connection at another location on the body, and a membrane system affixed to the body and covering the electroactive surface.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (such as, for example, $H_2O_2$) associated with the measured analyte (such as, for example, glucose). For example, in one embodiment, a sensor has a sensitivity of from about 1 to about 300 picoAmps of current for every 1 mg/dL of glucose analyte.

The term "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

The terms "sensor analyte values" and "sensor data," as used herein, are broad terms, and are to be given their ordinary and customary meaning to a person of ordinary skill in the art (and they are not to be limited to a special or customized meaning), and refer without limitation to data received from a continuous analyte sensor, including one or more time-spaced sensor data points.

The terms "sensor electronics" and "electronic circuitry," as used herein, are broad terms, and are to be given their ordinary and customary meaning to a person of ordinary skill in the art (and they are not to be limited to a special or customized meaning), and refer without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398 describe suitable electronic circuits that can be utilized with devices of certain embodiments.

The term "sensor environment" or "sensor operational environment," as used herein, are broad terms and are to be given their ordinary and customary meaning to a person of ordinary skill in the art (and is not to me limited to a special or customized meaning), and refer without limitation to the biological environment in which a sensor is operating.

The terms "substantial" and "substantially," as used herein, are broad terms, and are to be given their ordinary and customary meaning to a person of ordinary skill in the art (and are not to be limited to a special or customized meaning), and refer without limitation to being largely but not necessarily wholly that which is specified.

The term "thermal conductivity," as used herein, is a broad term, and is to be given its ordinary and customary meaning to a person of ordinary skill in the art (and it is not to be limited to a special or customized meaning), and refers without limitation to the quantity of heat transmitted, due to unit temperature gradient, in unit time under steady conditions in a direction normal to a surface of unit area.

The term "thermal coefficient," as used herein, is a broad term, and is to be given its ordinary and customary meaning to a person of ordinary skill in the art (and is not to be limited to a special or customized meaning), and refers without limitation to the change in resistance of a material at various temperatures.

The term "thermally conductive material," as used herein, is a broad term, and is to be given its ordinary and customary meaning to a person of ordinary skill in the art (and is not to be limited to a special or customized meaning), and refers without limitation to materials displaying a high degree of thermal conductivity.

The term "thermocouple," as used herein, is a broad term, and is to be given its ordinary and customary meaning to a person of ordinary skill in the art (and is not to be limited to a special or customized meaning), and refers without limitation to a device including two different conductors (such as, for example metal alloys) that produce a voltage, proportional to a temperature difference, between either ends of the two conductors.

The term "twisted," as used herein, is a broad term, and is to be given its ordinary and customary meaning to a person of ordinary skill in the art (and it is not to be limited to a special or customized meaning), and refers without limitation to united by having one part or end turned in the opposite direction to the other, such as, but not limited to the twisted strands of fiber in a string, yarn, or cable.

Overview

Devices, systems, and methods for determining a temperature compensation factor to account for changes in temperature of a sensor environment are provided. Conventional continuous analyte sensors lack the capability to detect and/or respond to temperature changes of the sensor environment. In some aspects, a method for determining a temperature compensation factor includes measuring the temperature of a sensor environment, a temperature change of the sensor environment, or some other property indicative of a temperature or temperature change of a sensor environment. A method for determining a temperature compensation factor may further include processing a temperature measurement of a sensor environment, as discussed more fully herein.

Generally, implantable sensors measure a signal (e.g., counts) related to an analyte of interest in a host. For example, an electrochemical sensor can measure glucose, creatinine, or urea in a host, such as an animal, especially a human. Generally, the signal can be converted mathematically to a numeric value indicative of analyte status, such as analyte concentration. In some embodiments, the analyte sensor can be an invasive, minimally invasive, or non-invasive device, for example a subcutaneous, transdermal or transcutaneous, or intravascular device. In some embodiments, the analyte sensor may analyze a plurality of intermittent biological samples. The analyte sensor may use any method of analyte-measurement, including enzymatic, chemical, physical, electrochemical, spectrophotometric, polarimetric, calorimetric, radiometric, or the like.

In general, electrochemical analyte sensors include at least one working electrode and at least one reference electrode that are configured to measure a signal associated with a concentration of the analyte in the host, such as described in more detail below, and as appreciated by one skilled in the art. In some embodiments, the sensor includes at least two working electrodes (such as, for example, one with enzyme over its electroactive surface and one without enzyme over its electroactive surface), and sensor electronics operably connected to the working and auxiliary electrodes. The analyte sensors can also include at least one additional working electrode configured to measure at least one additional signal. For example, in some embodiments, the additional signal can be associated with the baseline and/or sensitivity of the analyte sensor, thereby enabling monitoring of baseline and/or sensitivity changes that may occur in a continuous analyte sensor over time.

Preferably, each electrode can be formed from an elongated body, such as, for example, an elongated conductive body. The elongated conductive body may have a diameter (e.g., distance across a cross-section perpendicular to a longest dimension of the elongated conductive body) from about 0.001 inches to about 0.01 inches, such as, for example, from about 0.001 inches to about to about 0.009 inches, from about 0.001 inches to about 0.008 inches, from about 0.001 inches to about 0.007 inches, from about 0.001 inches to about 0.006 inches, from about 0.001 inches to about 0.005 inches, from about 0.001 inches to about 0.004 inches, from about 0.001 inches to about 0.003 inches, from about 0.001 inches to about 0.002 inches, from about 0.002 inches to about to about 0.01 inches, from about 0.003 inches to about 0.01 inches, from about 0.004 inches to about 0.01 inches, from about 0.005 inches to about 0.01 inches, from about 0.006 inches to about 0.01 inches, from about 0.007 inches to about 0.01 inches, from about 0.008 inches to about 0.01 inches, or from about 0.009 inches to about 0.01 inches. In some embodiments, for example, the elongated conductive body may have a diameter (e.g., distance across a cross-section) equal to about less than 0.001 inches, about 0.001 inches, about 0.002 inches, about 0.003 inches, about 0.004 inches, about 0.005 inches, about 0.006 inches, about 0.007 inches, about 0.008 inches, about 0.009 inches, about 0.01 inches, or more than about 0.01 inches. In certain embodiments, the elongated conductive body may be formed from plated wire, composite wire, or bulk material. The length (e.g., distance along a longest dimension) of the elongated conductive body is typically longer than the diameter (e.g., distance across a cross-section), e.g., 1.5 times the diameter, or 2, 3, 4, 5, 6, 7, 8, 9, 10, 20, 30, 40, 50, 60, 70, 80, 90, 100, 125, 150, 175, 200, 250, or 300 or more times the diameter. In certain embodiments, the length can be shorter than the diameter.

According to some embodiments, the electrodes may be deposited on a substrate (e.g., conducting or nonconducting elongated body) or in other known configurations as is appreciated by one skilled in the art. The diameter (e.g., distance across a cross-section perpendicular to a longest dimension) of the electrode can be from about 0.001 inches to about 0.01 inches, such as, for example, from about 0.001 inches to about to about 0.009 inches, from about 0.001 inches to about 0.008 inches, from about 0.001 inches to about 0.007 inches, from about 0.001 inches to about 0.006 inches, from about 0.001 inches to about 0.005 inches, from about 0.001 inches to about 0.004 inches, from about 0.001 inches to about 0.003 inches, from about 0.001 inches to about 0.002 inches, from about 0.002 inches to about to about 0.01 inches, from about 0.003 inches to about 0.01 inches, from about 0.004 inches to about 0.01 inches, from about 0.005 inches to about 0.01 inches, from about 0.006 inches to about 0.01 inches, from about 0.007 inches to about 0.01 inches, from about 0.008 inches to about 0.01 inches, or from about 0.009 inches to about 0.01 inches. In some embodiments, for example, the electrode may have a diameter equal to less than about 0.001 inches, about 0.001 inches, about 0.002 inches, about 0.003 inches, about 0.004 inches, about 0.005 inches, about 0.006 inches, about 0.007 inches, about 0.008 inches, about 0.009 inches, about 0.01 inches, or more than about 0.01 inches. The length (e.g., distance along a longest dimension) of the electrode is typically longer than the diameter (e.g., distance across a cross-section), e.g., 1.5 times the diameter, or 2, 3, 4, 5, 6, 7, 8, 9, 10, 20, 30, 40, 50, 60, 70, 80, 90, 100, 125, 150, 175, 200, 250, or 300 or more times the diameter. In certain embodiments, the length can be shorter than the diameter.

FIG. 1 schematically illustrates the in vivo portion of a dual-electrode analyte sensor. For example, the sensor can comprise first and second elongated bodies (such as, for example, conductive cores) E1, E2. Further, a working electrode can comprise an exposed electroactive surface of the elongated body and a reference electrode 114. The reference electrode can be bundled together with the first and second elongated bodies E1, E2, for example. Moreover, each working electrode can comprise a conductive core. For example, the first working electrode can comprise an exposed portion of the surface of a first elongated body 102A having an insulating material 104A disposed thereon, such that the portion of the surface of the elongated body (that is, the working electrode) is exposed via a radial window 106A in the insulator. The insulating material 104A can comprise a polymer, such as, for example, a non-conductive (that is, dielectric) polymer. The insulating material can include, for example, at least one of polyurethane, polyimide or parylene. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material, such as, but not limited to, a dielectric ink, paste or paint, can be used, for example, fluorinated polymers, polyethyleneterephthalate, polyurethane, polyimide, other non-conducting polymers, or the like. In some embodiments, glass or ceramic materials can also be employed.

The elongated body may comprise a core and a first layer, wherein an exposed (that is, electroactive) surface of the first layer is the first working electrode. The second working electrode can comprise an exposed surface of a elongated body 102B having an insulator 104B disposed thereon, such that a portion of the surface of the elongated body is exposed via a radial window 106B in the insulator. A first layer (not shown) can be applied to the exposed surface of the second core to form the second working electrode. Accordingly, the radial windows can be spaced such that the working electrodes (that is, the electroactive surfaces) are substantially overlapping along the length of the sensor. However, in other embodiments, the working electrodes can be spaced such that they are not substantially overlapping along the length of the sensor. According to certain embodiments, the reference electrode can comprise a wire (such as, for example, Ag/AgCl wire) wrapped around the bundled conductive cores. Alternatively, the reference electrode can comprise a layer of silver-containing material applied to at least one of the conductive cores.

As further shown in FIG. 1, one or more connectors can be configured and arranged to hold the conductive cores and reference electrode together. For example, a tube 130 or heat shrink material can be employed as a connector and/or supporting member. The tubing or heat shrink material may include an adhesive inside the tube so as to provide enhanced adhesion to the components secured within (such as, for example, wire(s), core, layer materials, etc.). In such a configuration, the heat-shrink material functions not only as an insulator, but also to hold the proximal ends of the sensor together so as to prevent or reduce fatigue and/or to maintain the electrodes together in the event of a fatigue failure. The wires need not be a core and a layer, but can instead comprise bulk materials.

The distal ends of the sensor can be loose and finger-like, as depicted in FIG. 1, for example. Alternatively, the distal ends of the sensor can be held together with an end cap. A reference electrode can be placed on one or more of the first and second elongated bodies instead of being provided as a separate electrode, and the first and second elongated bodies including at least one reference electrode thereof can be bundled together. Heat shrink tubing, crimp wrapping, dipping, or the like can be employed to bundle one or more elongated bodies together. In some embodiments, the reference electrode is a wire, such as described elsewhere herein. In other embodiments, the reference electrode comprises a foil. In an embodiment of a dual-electrode analyte sensor, the first and second elongated bodies can be present as or formed into a twisted pair, which is subsequently bundled with a wire or foil reference electrode. Connectors, which can also function as supporting members, can be configured and arranged to hold the conductive cores and reference electrode together.

Figure 2C:
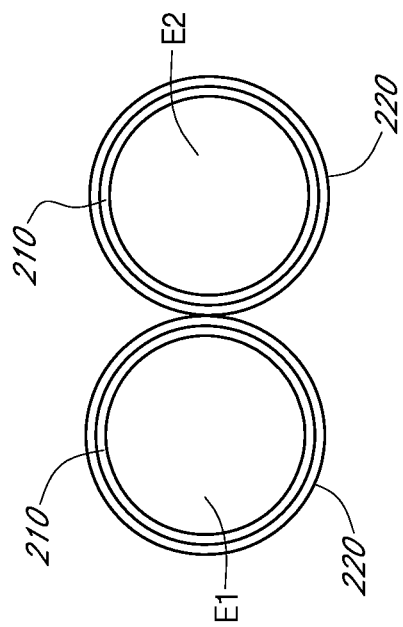
FIG. 2C is a front view of the sensor embodiment illustrated in FIGS. 2A and 2B.
Figure 2B:
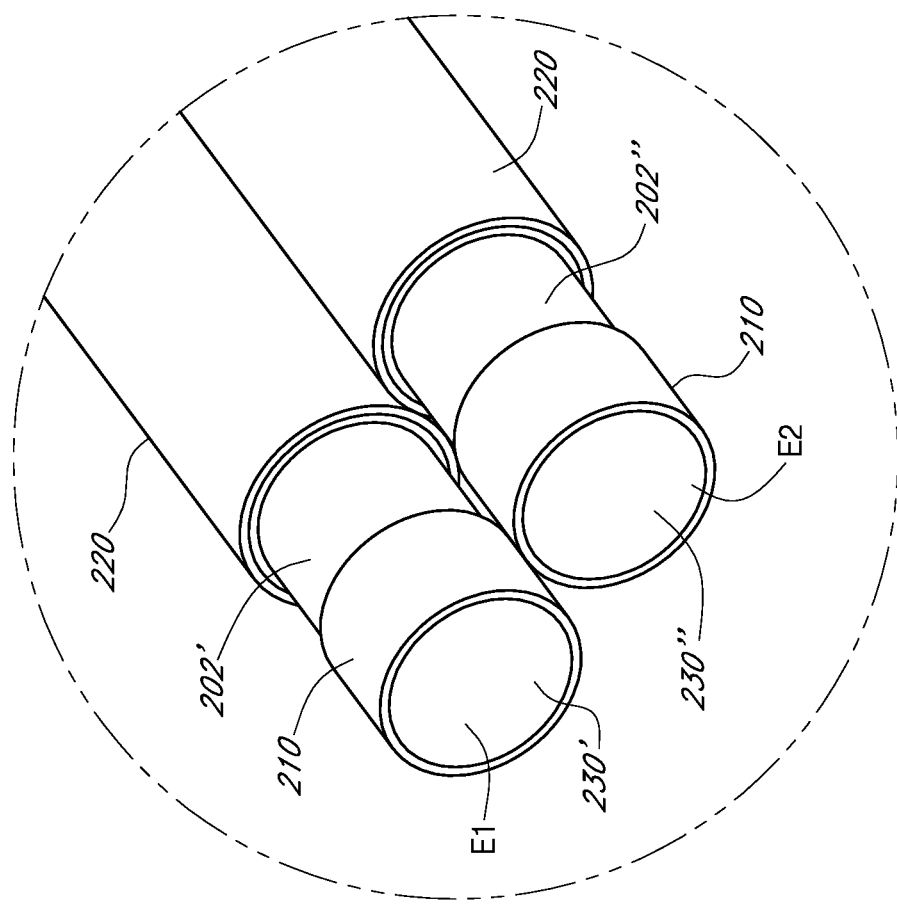
FIG. 2B is a close perspective schematic of the distal portion of the sensor embodiment illustrated in FIG. 2A.

FIG. 2A is a perspective view of the in vivo portion of a multi-electrode sensor system 200. The electrode system 200 may comprise two working electrodes and at least one reference/counter electrode. The sensor system 200 comprises first and second elongated bodies E1, E2. The first and second elongated bodies E1, E2 each can be formed of a conductive core. Alternatively, the first and second elongated bodies E1, E2 can be formed of a core with a conductive layer deposited thereon. As shown in FIG. 2A, for example, an insulating layer 210, a conductive layer 220, and a membrane layer (not shown) can be deposited on top of the first and second elongated bodies E1, E2. The insulating layer 210 can separate the conductive layer 220 from the elongated body. The materials selected to form the insulating layer 210 may include any of the insulating materials described elsewhere herein. For example, the insulating layer can comprise a non-conductive polymer, such as, polyurethane or polyimide. The materials selected to form the conductive layer 220 may include, for example, platinum, platinum-iridium, gold, palladium, iridium, graphite, carbon, a conductive polymer, an alloy, and the like. Working electrodes 202', 202" can be formed by removing a portion of the conductive layer 220 and the insulating layer 210, thereby exposing an electroactive surface of the first and second elongated bodies E1, E2. FIG. 2B provides a close perspective view of the distal portion of the elongated bodies E1, E2. FIG. 2C provides a front view of the sensor illustrated in FIGS. 2A and 2B.

The two elongated bodies illustrated in FIG. 2A can be fabricated to have substantially the same shape and dimensions. According to certain embodiments, the working electrodes can be fabricated to have the same properties, thereby providing a sensor system capable of providing redundancy of signal measurements. In other embodiments, the working electrodes, associated with the elongated bodies E1, E2, may each have one or more characteristics that distinguish each working electrode from the other. For example, in one embodiment, each of the elongated bodies E1, E2 may be covered with a different membrane, so that each working electrode has a different membrane property than the other working electrode. For example, one of the working electrodes may have a membrane comprising an enzyme layer and the other working electrode may have a membrane comprising a layer having either an inactivated form of the enzyme or no enzyme.

Although not shown in FIGS. 2A-2C, The distal ends 230', 230" of the core portions of the elongated bodies E1, E2, respectively, can be covered with an insulating material (such as, for example, polyurethane or polyimide). Alternatively, the exposed core portions 230', 230" can be covered with a membrane system and serve as additional working electrode surface area.

Figure 3A:
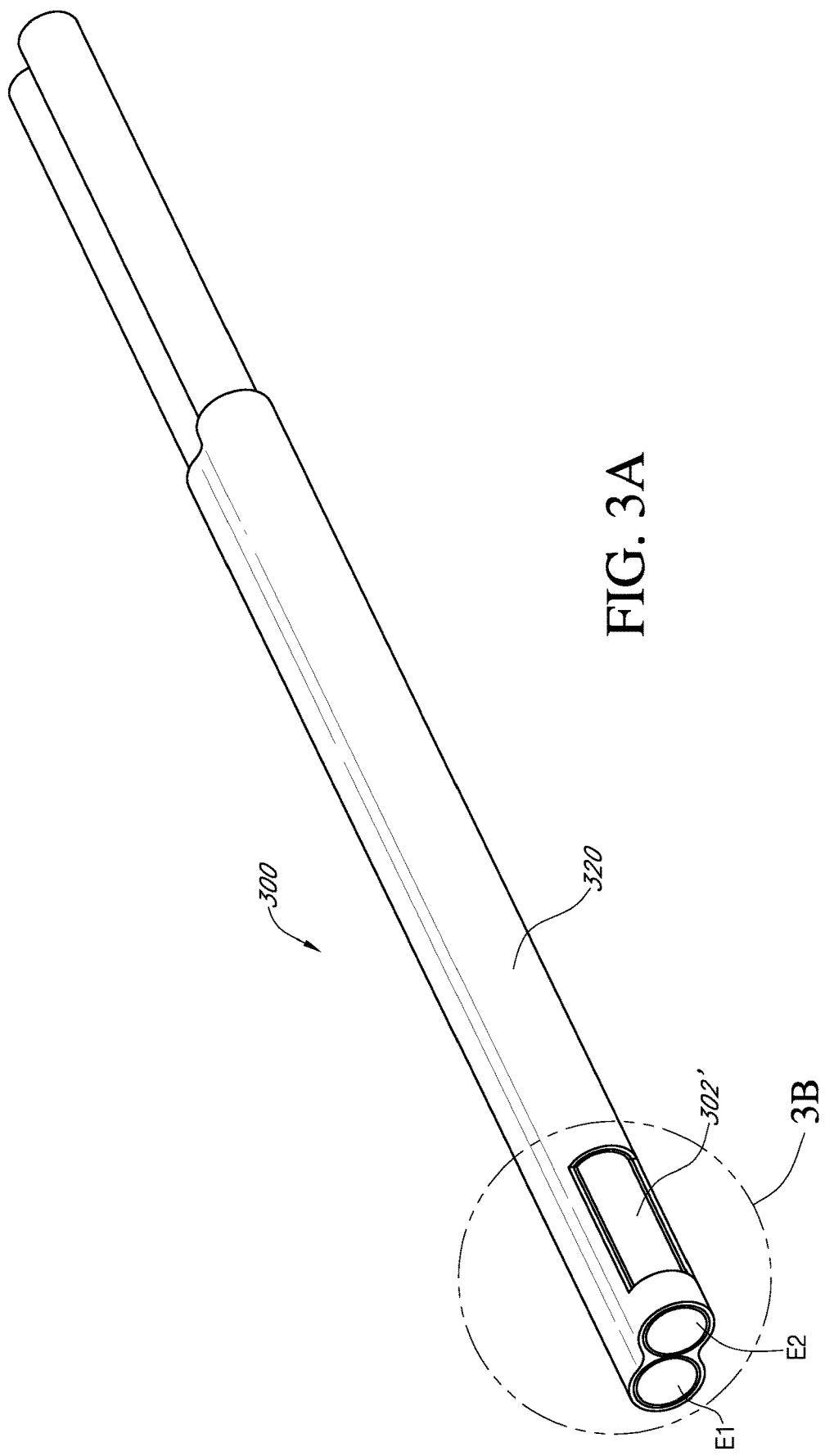
FIG. 3A is a perspective-view schematic illustrating an in vivo portion of a multi-electrode analyte sensor, in another embodiment.
Figure 3C:
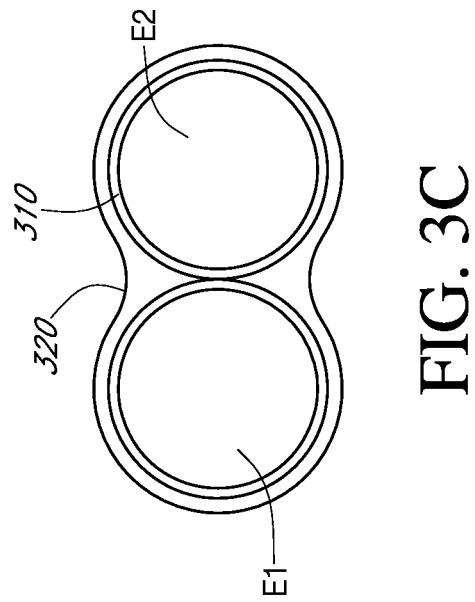
FIG. 3C is a front view of the sensor embodiment illustrated in FIGS. 3A and 3B.
Figure 3B:
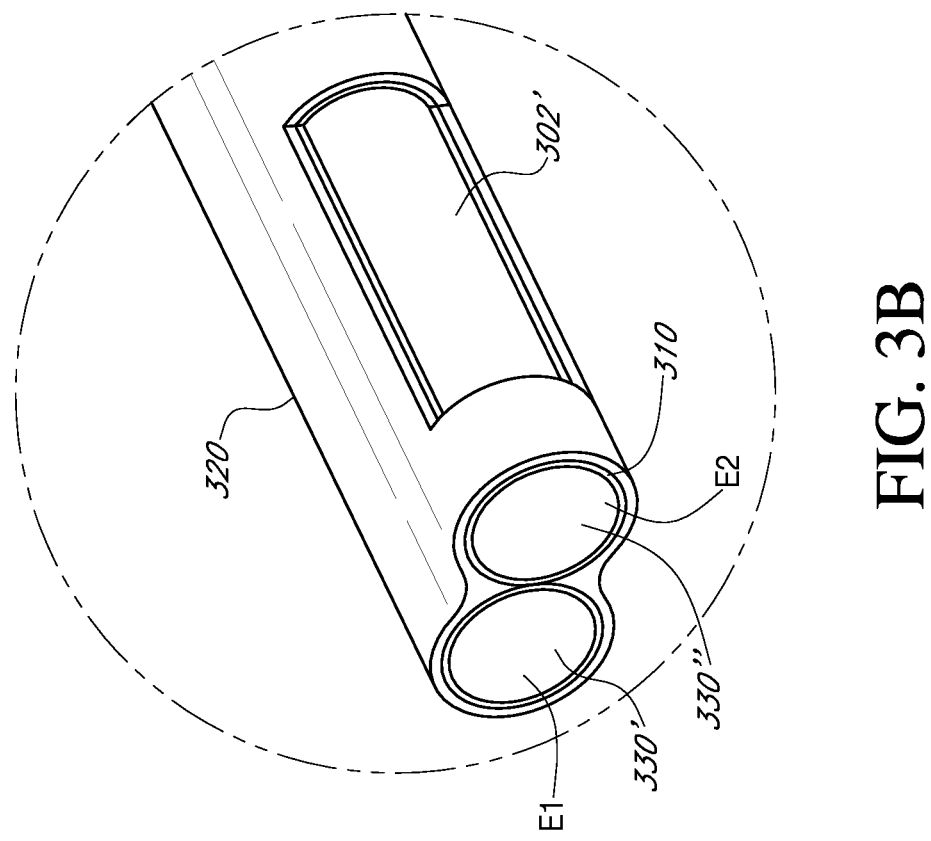
FIG. 3B is a close perspective schematic of the distal portion of the sensor embodiment illustrated in FIG. 3A.

FIG. 3A is a perspective view of the in vivo portion of an embodiment of a multi-electrode sensor system 300 comprising two working electrodes and at least one reference/counter electrode. The sensor system 300 comprises first and second elongated bodies E1, E2. First and second elongated bodies, E1, E2 each can be formed of a conductive core. Alternatively, first and second elongated bodies E1, E2 can be formed of a core with a conductive layer deposited thereon. An insulating layer 310 can be deposited onto each elongated body E1, E2. Furthermore, a conductive domain 320 and a membrane layer (not shown) can be deposited on top of an assembly comprising the elongated bodies E1, E2 and the insulating layer 310. The conductive domain 320 can bind the two elongated bodies E1, E2 into one elongated body. The insulating layers 310 surrounding each elongated body E1, E2 can prevent electrical contact between the two elongated bodies E1, E2. The materials selected to form the insulating layer 310 can include any of the insulating materials described elsewhere herein, including, for example, polyurethane and polyimide. The materials selected to form the conductive domain 320 can include any of the conductive materials described elsewhere herein, including, for example silver/silver-chloride and platinum. Working electrode 302' on elongated body E1 and another working electrode (not shown) on elongated body E2, can be formed by removing a portion of the conductive domain 320 and a portion of the insulating layer 310, thereby exposing electroactive surfaces of elongated bodies E1, E2. The portion of the conductive domain 320 not removed can form the reference/counter electrode. FIG. 3B provides a close perspective view of the distal portion of the elongated bodies E1, E2. FIG. 3C provides a front view of the sensor embodiment illustrated in FIGS. 3A and 3B.

As described elsewhere herein, the working electrodes, associated with the elongated bodies E1, E2, may each have one or more characteristics that distinguish each working electrode from the other. For example, in some embodiments, one of the working electrodes may have a membrane comprising an enzyme layer and the other working electrode may have a membrane comprising a layer having either an inactivated form of the enzyme or no enzyme.

Although not shown in FIGS. 3A-3C, The distal ends 330', 330" of the core portions of the elongated bodies E1, E2, respectively, can be covered with an insulating material (such as, for example, polyurethane or polyimide). Alternatively, one or more of the exposed core portions 330', 330" may be covered with a membrane system and serve as additional working electrodes.

Methods of fabrication of the sensor systems illustrated in FIGS. 2A-2C and 3A-3C are described in U.S. Patent Publication No. 2011-0027127, which is incorporated by reference herein in its entirety.

Electrodes and sensors can be configured to measure and detect various in vivo properties and physiological changes and conditions. Such electrodes and sensors can also be coupled with or integrated with or in communication with devices or systems that measure and detect various in vivo properties and physiological conditions. Examples of such various sensor systems are described in U.S. Patent Publication No. 2011-0024307, which is herein incorporated by reference in its entirety.

According to certain embodiments, a sensor system can be provided for continuous measurement of an analyte (such as, for example, glucose) in a host that includes: a continuous analyte sensor configured to continuously measure a concentration of the analyte in the host and a sensor electronics module operably connected to the continuous analyte sensor during sensor use. For example, a continuous glucose sensor may be provided for continuous glucose sensing. The sensor electronics module can include electronics configured to process a data stream associated with an analyte concentration measured by the continuous analyte sensor in order to process the sensor data and generate displayable sensor information that includes, for example, raw sensor data, transformed sensor data, and/or any other sensor data. The sensor electronics module can include a processor and computer program instructions to implement the processes discussed herein. For example, the sensor electronics can include, among other components, a potentiostat, A/D converter, RAM, ROM, transceiver, processor, and/or the like. The potentiostat may be used to provide a bias to the electrodes and to convert the raw data (e.g., raw counts) collected from the sensor to an analyte concentration value (e.g., a glucose concentration value expressed in units of mg/dL). The transmitter may be used to transmit the first and second signals to a receiver, where additional data analysis and additionally or alternatively calibration of analyte concentration can be processed. Moreover, the sensor electronics may perform additional operations, such as, for example, data filtering and noise analysis.

According to certain embodiments, a receiver, which can also be referred to as a display device, or can include a display device, can be in communication with the sensor electronics module (such as, for example, via wired or wireless communication). An electronics module, e.g., sensor electronics module or other type of module, can comprise or include or one or more various components such as a "processor" or a "processing module", and can be referred to in abbreviated form as "electronics" in some embodiments. The receiver can be an application-specific hand-held device. Alternatively, the receiver can be a general purpose device, such as, for example, a personal computer (PC), smart phone, tablet computer, or the like. The receiver can be in data communication with the sensor electronics module for receiving sensor data, such as raw data and additionally or alternatively displayable data. Furthermore, the receiver can include a processing module for processing the received sensor data and additionally or alternatively displaying the received sensor data. The receiver can also include an input module configured to receive input, such as calibration codes, reference analyte values, and any other information discussed herein, from a user via a keyboard or touch-sensitive display screen, for example. The input module can also be configured to receive information from external devices, such as insulin pumps and reference meters, via wired or wireless data communication. The input can be processed alone or in combination with information received from the sensor electronics module. The receiver's processing module can include a processor and computer program instructions to implement any of the processes discussed herein.

Measuring Change in Temperature

A method for real-time or dynamic temperature compensation can include determining a temperature of a sensor environment (indicative of the sensor's temperature) or the sensor itself. A method for real-time or dynamic temperature compensation can further include determining a change in temperature of a sensor environment (indicative of the sensor's temperature) or the sensor itself. That is, the temperature determined by a sensor can be either an absolute temperature or a difference in temperature, or the temperature or difference in temperature can be determined by measuring another property that is indicative of the temperature or difference in temperature, as described herein. A variety of techniques and configurations are provided that can be used to determine a sensor temperature. The temperature determination can then be used to calculate a temperature compensation factor, according to the methods and techniques discussed further herein. The temperature compensation factor can be used to scale sensor data. The temperature compensation factor can be used to scale either one or both of measured (such as, for example, raw) sensor data or processed sensor data. According to certain embodiments, scaled sensor data can reflect a more accurate representation of the value measured by the sensor. For example, by scaling sensor data, a more accurate analyte (such as, for example, glucose) concentration can be determined. The scaled analyte value can be provided by the sensor electronics as an output to the user. Alternatively, or additionally, the scaled analyte value can be utilized by the sensor electronics for a variety of purposes. For example, the scaled analyte value can be used to more accurately control delivery of insulin by an insulin pump integrated with the sensor.

In one embodiment, temperature changes can be measured by a system having two or more electrodes which respond differently to a change in temperature. In the case of sensor electrodes equipped with sensor membranes, the sensor membranes can have varying temperature coefficients based on the material or materials included in the membrane. For example, polyurethane (PU) has a different temperature coefficient than silicone polycarbonate urethane. In one embodiment, a potential difference between the electrodes can be measured, wherein the magnitude of the potential difference is indicative of an absolute temperature. Alternatively, the potential between the electrodes can be varied, and current differences measured, with a magnitude of the current difference correlating to a particular temperature. A lookup table can be stored by the processor, with a particular potential difference or current difference correlating to a particular temperature.

In practice, a first electrode can have a first membrane and a second electrode can have a second, different (e.g., in terms of composition, thickness, porosity, permeability, hydrophilicity, hydrophobicity, etc.) membrane. The first membrane can include of a first material having a temperature coefficient that is different than a temperature coefficient of a second material included in the second membrane. The difference in temperature coefficient between the first and second materials can be at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, greater than about 100%, greater than about 150%, or greater than about 200%. A smaller difference between the temperature coefficients of the first and second materials may also be acceptable. For example, the difference in temperature coefficient between the first and second materials can be less than about 5%, about 4%, about 3%, about 2%, about 1.5%, about 1%, about 0.75%, about 0.5%, about 0.25%, or less than about 0.1%.

The thermal coefficient of a sensor membrane comprising a particular polymeric component can depend, at least in part, on the content of that particular polymeric component in the membrane. In the case of a silicone membrane, the silicone content of the membrane can impact the thermal coefficient. Accordingly, the polymer content, e.g., silicone content, of a first membrane can be different than the polymer content, e.g., silicone content, of a second membrane. For example, the difference in polymer content, e.g., silicone content, between the first membrane and the second membrane can be at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, greater than about 100%, greater than about 150%, or greater than about 200%.

As described above, a silicone sensor membrane can be made to be thermally responsive by, for example, changing the silicone content therein. Changing the silicone content can, for example, affect the membrane resistance and/or membrane permeability. Accordingly, a first electrode can be provided with a first membrane comprised at least in part of silicone, and a second electrode can be provided with a second membrane comprised at least in part of silicone, but at a different concentration. By varying the relative silicone content of a first membrane and a second membrane, the effect of a change in temperature of the sensor environment can be examined. In certain embodiments, the silicone content of a first membrane can be from about 1% to about 50%, from about 5% to about 45%, from about 10% to about 40%, from about 15% to about 35%, from about 20% to about 30%, or about 25%. Furthermore, the silicone content of the second membrane can be different from that of the first membrane and from about 50% to about 100%, from about 55% to about 95%, from about 60% to about 90%, from about 65% to about 85%, from about 70% to about 80%, or about 75%. For example, the silicone content of the first membrane can be about 20% and the silicone content of the second membrane can be about 70%.

The correlation between membrane resistance and temperature for a particular sensor or sensors can be stored in the sensor electronics. Therefore, the membrane resistance can be measured and a corresponding temperature of the sensor environment can be recalled from stored data in the sensor electronics. Alternatively, look-up tables correlating membrane resistance to temperature can be used to determine the temperature for a measured resistance value. In such embodiments, for example, the sensor can display the membrane resistance as an output. A user can then use membrane resistance value to find a corresponding temperature value. In some embodiments, the user can provide the temperature value determined by reference to the look-up table as an input to the sensor. Look-up tables can be employed to contain any information regarding a correlation of a measurement of a temperature-dependent property, e.g., potential difference between two electrodes as described herein having different responses to temperature as described herein, to an actual in vivo temperature, and an appropriate temperature compensation factor can be applied to the measurement of glucose concentration or other analyte concentration to obtain a more accurate concentration value.

During the early stages after sensor implantation, it is expected that baseline and/or sensor sensitivity values may change between sensor calibrations. Thus, as time passes after calibration using one or more reference analyte values (e.g., analyte values obtained from a self-monitored blood analyte test, such as a finger stick test), the resulting calculated sensor values (using a particular conversion function determined at the calibration) may differ from substantially time-corresponding blood glucose (BG) values due to changes of the sensor and/or its surrounding environment. This phenomenon is referred to as "drift," and is due at least in part to the fact that the sensor may undergo a time-dependent shift in baseline sensitivity after implantation. Accordingly, to provide for more accurate sensor values between calibrations, drift is preferably taken into consideration by applying appropriate compensation.

Drift can occur at either the beginning or end of a sensor's lifespan. For example, a rate of increase in sensor sensitivity may typically be greatest in the early stages after sensor implantation, and may span the first day up to about three days after sensor implantation, but could last more or less time. For example, a rate of increase in sensor sensitivity may span the first six, eight, ten, twelve, eighteen, twenty-four, forty-eight, seventy-two or ninety-six hours, or more, after implantation. Eventually, the sensor sensitivity levels off. Furthermore, sensor sensitivity begins to decrease as the sensor reaches the end of its usable life.

Accordingly, a compensation function for the change in sensitivity (i.e., drift curve) can be applied to measured sensor data to provide for more accurate sensor values between calibrations. Accuracy of measurements can therefore be further enhanced by applying both a temperature compensation factor according to any of the methods disclosed herein and a drift compensation function. In some embodiments, accuracy of measurements can be enhanced by using low drift sensors that are configured to measure temperature in accordance with any of the methods disclosed herein to determine a temperature compensation factor. Low drift sensors can be resistant to undergoing changes in baseline sensitivity after implantation or near the end of the sensor's lifespan. With low drift sensors, for example, an absolute change in sensitivity at either the beginning or end of the sensor's lifespan will be less than about 30%, about 25%, about 20%, about 15%, about 10%, about 5%, about 2.5%, or about 1%. Accordingly, by using low drift sensors in conjunction with the methods described herein to determine a temperature compensation factor, more accurate sensor values can be provided.

A temperature compensation factor can be determined, at least in part, on a change in temperature quantified by a sensor core functioning as a thermocouple. A sensor core may function as a thermocouple when two materials having a difference in conductance are joined together (such as, for example, when two dissimilar metals or metal alloys are joined together). By joining together two materials having a difference in conductance, an electric potential (voltage) related to temperature will be produced across the junction of the materials. The temperature-dependent change in voltage produced across the junction of the two materials can be quantified so that a measured voltage across the sensor core can be used to determine the change in temperature. Accordingly, any standard or thermocouple can be used in conjunction with an analyte sensor to determine the temperature in a sensor environment according to the Seebeck effect.

Accordingly, a sensor core can be fabricated to function as a thermocouple by joining together a first elongated conductive body having a first conductance with a second elongated conductive body having a second conductance. Moreover, either one or both of the first elongated conductive body and the second elongated conductive body may include any one or more of aluminum, aluminum oxide, beryllium, brass, cadmium, carbon steel, chromium, cobalt, copper, gold, iridium, iron, lead, magnesium, molybdenum, nickel, platinum, rhodium, silicon, silver, tantalum, tin, tungsten, zinc, or zirconium. For example, either the first elongated conductive body or the second elongated conductive body can include tantalum.

The conductance of the first elongated conductive body can be different from the conductance of the second elongated conductive body. For example, the first conductance can be greater than the second conductance. Alternatively, the first conductance can be less than the second conductance. The absolute difference between the first conductance and the second conductance can be, for example, less than about 5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more than about 100%.

The correlation between electrical potential and temperature for a particular thermocouple included in a sensor can be stored in the sensor electronics. Therefore, when the voltage across the junction of the elongate body is measured, the corresponding temperature of the sensor environment can be recalled from stored data in the sensor electronics. Alternatively, look-up tables correlating voltage to temperature can be used to determine the temperature for a voltage drop across the junction of a thermocouple. For example, the sensor can display the voltage drop across the junction of the elongated body. A user can use this value to find a corresponding temperature value. In some embodiments, the user can provide the temperature value determined by reference to the look-up table as an input to the sensor.

A sensor can include an elongated body, wherein the elongated body can include a shape memory material. For example, the sensor core can be an elongated body that includes a shape memory material. Moreover, the shape memory material can be a shape memory alloy. For example, the elongated body can include an alloy containing two or more of aluminum, cobalt, copper, gold, iron, manganese, nickel, silicon, titanium, zinc, or any other alloying members known to those of skill in the art that are suitable to produce alloys with shape memory capabilities. The elongated body can include a copper-aluminum-nickel alloy, a copper-zinc-aluminum alloy, an iron-manganese-silicon alloy, a nickel-titanium alloy, or any other alloys known to those of skill in the art having suitable shape memory characteristics.

The elongated body can include a nickel-titanium alloy (such as, for example, NITINOL®). The nickel-titanium alloy can include an amount of nickel, for example, from about 40% to about 70% by weight, from about 45% to about 65% by weight, from about 50% to about 60% by weight, or about 55% by weight. Furthermore, the balance of the composition of the nickel titanium alloy can be titanium. For example, the nickel-titanium alloy can include an amount of titanium from about 30% to about 60% by weight, from about 35% to about 55% by weight, from about 40% to about 50% by weight, or about 45% by weight. Additionally, the nickel-titanium alloy may include additional elements. Additional elements contained in a nickel-titanium alloy can modify, for example, the transitional temperature range and additionally or alternatively other mechanical properties of the alloy. For example, the nickel-titanium alloy composition can include nickel and titanium substantially as described above, and can further include cobalt. The nickel-titanium alloy can include an amount of cobalt from about 1% to about 2.5% by weight, from about 1.1% to about 2.25% by weight, from about 1.2% to about 2% by weight, from about 1.3% to about 1.9% by weight, from about 1.4% to about 1.8% by weight, from about 1.5% to about 1.7% by weight, or about 1.6% by weight. For example, the nickel-titanium alloy can be composed of about 53.5% by weight of nickel, about 44.9% by weight of titanium, and about 1.6% by weight of cobalt.

The shape memory material of the elongated body can be a shape memory polymer. For example, the shape memory polymer may include a polynorbornene based polymer, a poly(trans-isoprene) based polymer, a polystyrene-butadiene based polymer, a polyurethane based polymer, a polyethylene terephthalate based polymer, a polyethylene oxide based polymer, a polyester based polymer, or any other polymers known to those of skill in the art having suitable shape memory characteristics.

Shape memory materials are capable of changing mechanical characteristics, such as, for example, shape, in response to changes in temperature. Thus, a sensor including an elongated body comprised of a shape memory material may change shape in response to a change in temperature.

A portion of a sensor (such as, for example, a sensor core) can be fabricated by forming a shape memory materials into a substantially linear shape at a temperature below the transition temperature of the shape memory material. Moreover, a shape memory material having a transition temperature substantially equal to or less than the average sensor operational environment (such as, for example, about 37° C.) can be selected. The transition temperature of the shape memory material for use with the elongated body of the sensor can be, for example, from about 20° C. to about 40° C., from about 25° C. to about 40° C., from about 30° C. to about 40° C., from about 35° C. to about 40° C., from about 20° C. to about 35° C., from about 20° C. to about 30° C., from about 20° C. to about 25° C., or overlapping ranges thereof. In use, therefore, the shape memory material included as the elongated body can change shape as the elongated body is heated to the temperature of the sensor environment. For example, as the shape memory material is heated to the temperature of the sensor environment, the shape memory material can transition into a substantially curved shape. Accordingly, the sensor core can include a shape memory material so that the sensor core can transition from a substantially linear shape when below the transition temperature to a substantially curved shape when heated above the transition temperature.

Generally, the amount or degree to which the shape memory material changes shape can be dependent on the temperature. For example, the more the temperature increases above the transition temperature, the more curved the shape memory material becomes. Alternatively, as the temperature decreases toward the transition temperature, the shape memory material will begin to straighten out into a more linear shape. In use, therefore, as the sensor operational environment fluctuates, the shape memory material included in the elongated body can change shape in response. For example, when the temperature of the sensor environment increases, the elongated body becomes more curved in response. Alternatively, when the temperature of the sensor environment decreases, the elongated body becomes less curved, that is, the elongate body becomes substantially more linear.

Accordingly, a strain gage in combination with a Wheatstone bridge can be included with a sensor having at least a portion, such as an elongated body, containing a shape memory material to measure force deflection as the elongated body changes shape. For example, as the temperature of the sensor environment increases and the elongated body becomes more curved, as discussed above, the strain gage can convert the force from the curvature of the elongated body into an electrical resistance. This electrical resistance can be determined using, for example, a Wheatstone bridge. Alternatively, as the temperature of the sensor environment decreases and the elongated body becomes less curved, the force on the elongated body can decrease. The decrease in force can be measured with, for example, the strain gage and Wheatstone bridge. Therefore, by quantifying the relationship between force and temperature for a particular elongated body containing a particular shape memory material, the temperature of the sensor environment can be determined based, at least in part, on the measurement of the force deflection of the elongated body.

The correlation between force and temperature for a particular sensor can be stored in the sensor electronics. Therefore, when the force deflection of the elongate body is measured by, for example, the strain gage-Wheatstone bridge combination, the corresponding temperature of the sensor environment can be recalled from stored data in the sensor electronics. Alternatively, look-up tables correlating force to temperature can be used to determine the temperature for a measured force. For example, the sensor can display the force deflection of the elongated body as it changes shape in response to a change in temperature of the sensor environment. A user can then use this force value to find a corresponding temperature value. Furthermore, the user can provide the temperature value determined by reference to the look-up table as an input to the sensor.

Moreover, a shape memory material can be used in Wheatstone bridge style with a doped transducer built onto an elongated conductive body. Thus, resistance can change in response to a change in geometry or the shape memory material. Accordingly, a correlation between resistance and temperature for a particular sensor can be determined. The resistance-temperature relationship can be stored in sensor electronics, for example. Therefore, when a resistance is measured, the corresponding temperature of the sensor environment can be recalled from stored data in the sensor electronics. Alternatively, look-up tables correlating resistance to temperature can be used to determine the temperature for a measured resistance. For example, the sensor can display the measured resistance and a user can use this value to find a corresponding temperature value. In some embodiments, the user can provide the temperature value determined by reference to the look-up table as an input to the sensor.

An analyte sensor can determine a temperature compensation factor or value based, at least in part, on a temperature determined by a fiber optic temperature sensor. For example, a fiber optic temperature sensor may be included in the analyte sensor to determine the temperature of the sensor environment. The fiber optic temperature sensor can be configured in any manner known to those of skill in the art. Moreover, the sensor core can comprise a fiber optic temperature sensor to determine temperature of a sensor environment. The fiber optic temperature sensor can be operably connected to sensor electronics. Accordingly, a temperature determined by a fiber optic temperature sensor can be used, as described further herein, to determine a temperature compensation factor.

A state of particular properties, such as temperature, of a sensor can be determined by applying a stimulus signal of a particular frequency to the sensor and determining a sensor impedance based on the signal response. Furthermore, a stimulus signal containing a plurality of frequencies can be applied to the sensor to determine a sensor impedance based on the signal response.

Figure 4:
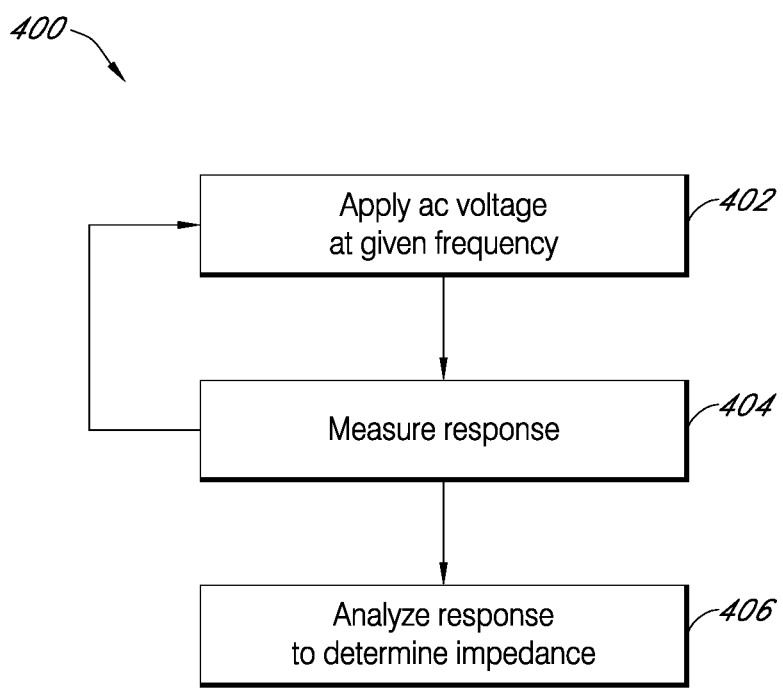
FIG. 4 is a flowchart describing a process for determining an impedance of a sensor in accordance with one embodiment.

With reference to FIG. 4, a flowchart is shown illustrating a process 400 for determining an impedance of a sensor in accordance with the various embodiments. At step 402, a stimulus signal in the form of an active current (ac) voltage at a given frequency can be applied to a working electrode of the sensor being studied. The ac voltage can be overlayed on a bias potential and can be relatively small as compared to the bias potential, such as a voltage that can be in the range of about 1% to 10% of the bias voltage. Moreover, the ac voltage can be a sine wave having an amplitude in the range of 10-50 mV and a frequency of from about 100 kHz to about 1 kHz. The sine wave can be overlayed on a 600 mV bias voltage. The response signal (e.g., in units of current) can then be measured in step 404 and analyzed in step 406 to determine an impedance at the given frequency. Should the impedance of the sensor at a range of frequencies be of interest, process 400 can be repeated by applying an ac voltage at each frequency of interest and analyzing a corresponding output response.

Figure 5:
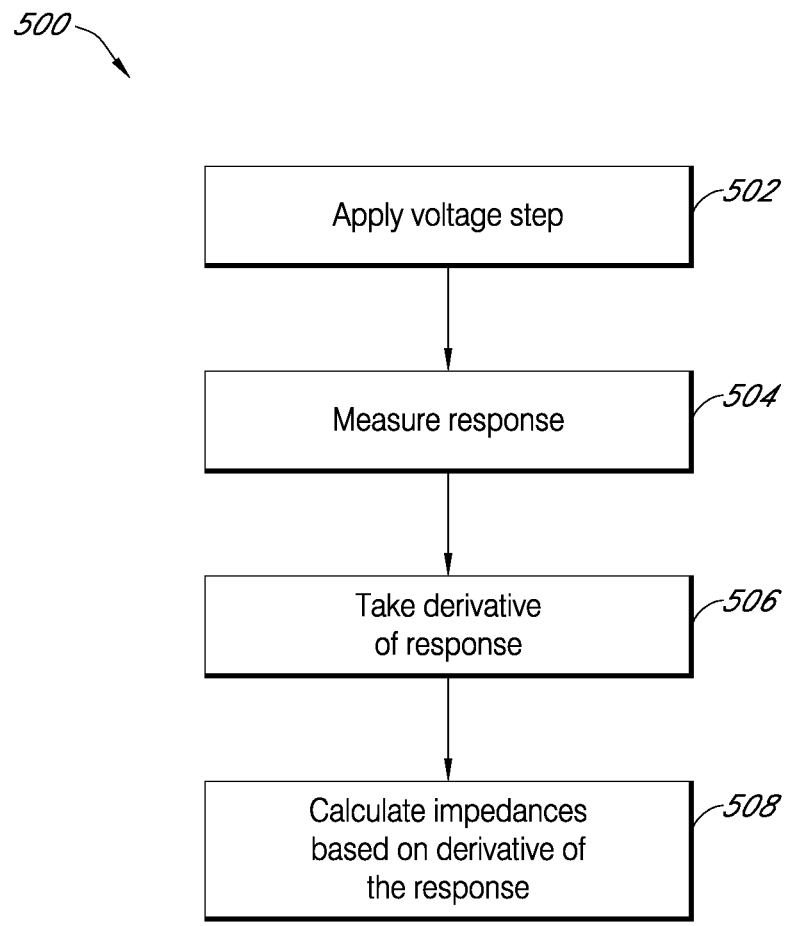
FIG. 5 is a flowchart describing a process for determining an impedance of a sensor based on a derivative response in accordance with one embodiment.

Reference will now be made to FIG. 5, which describes a process 500 for determining an impedance or plurality of impedances of a sensor being studied by applying one or more stimulus signals and converting the response signal or signals to a frequency domain in accordance with various embodiments. The data can be converted to the frequency domain using a Fourier transform technique. For example, a fast Fourier transform (FFT), discrete time Fourier transform (DTFT) or the like can be used to convert data to the frequency domain. At step 502, a stimulus signal in the form of, for example, a voltage step can be applied to a bias voltage of the sensor. The voltage step can be from about 10 mV to about 50 mV, from about 20 mV to about 50 mV, from about 30 mV to about 50 mV, from about 40 mV to about 50 mV, from about 10 mV to about 40 mV, from about 10 mV to about 30 mV, from about 10 mV to about 20 mV, or overlapping ranges thereof. For example, the voltage step can be about 10 mV, and the bias voltage can be about 600 mV. The signal response can then be measured and recorded (e.g., an output current) at step 504, and a derivative of the response can be taken at step 506. At step 508, a Fourier transform of the derivative of the response can then be calculated to yield ac currents in the frequency domain. One or more impedances of the sensor over a wide spectrum of frequencies can be calculated based on the ac currents measured at step 504.

Figure 6:
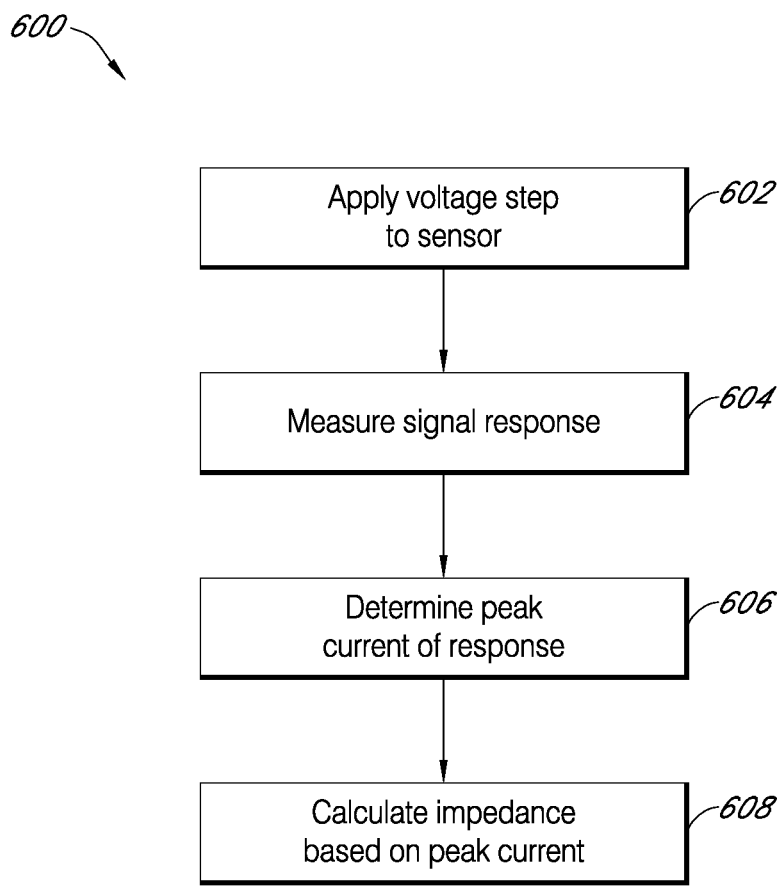
FIG. 6 is a flowchart describing a process for determining an impedance of a sensor based on a peak current response in accordance with one embodiment.

FIG. 6 is a flowchart of process 600 for determining an impedance of a sensor being studied. For example, process 600 can be used to determine the impedance of the sensor's membrane. At step 602, a stimulus signal in the form of a voltage step above a bias voltage can be applied to the sensor. The signal response can be measured at step 604, and, at step 606, a peak current of the response can be determined. At step 608, one or more impedance characteristics (such as, for example, resistance) of the sensor membrane (e.g., $R_{membrane}$) can be calculated based on the peak current. The one or more impedance characteristics can then be correlated to a property of the sensor. Accordingly, signal processing techniques can be used to determine a temperature of the sensor based on impedance characteristics. For example, a stimulus signal can be applied to a sensor and a signal response measured. Based on the signal response, a temperature of the sensor can be derived.

An impedance of a sensor membrane, as determined using any of the techniques described above with reference to FIGS. 4-6, for example, can be used to estimate a temperature of the sensor or sensor environment in accordance with various embodiments. Although not wishing to be bound by theory, it is believed that sensitivity of a sensor can be affected by temperature. For example, a higher temperature can result in a higher sensitivity and a lower temperature can result in a lower sensitivity. Similarly, because an impedance of a sensor membrane can have a direct relationship to the sensor's sensitivity, it is believed that a higher temperature can result in lower impedance and a lower temperature can result in higher impedance. That is, sensitivity and impedance can have a direct relationship to the sensor's temperature. Accordingly, using a known relationship between impedance and temperature, one can estimate a sensor's temperature based on a sensor impedance measurement. For example, based on previously conducted studies of substantially similar sensors, a determination of sensor impedance can be used to determine the temperature of the sensor or the sensor environment.

Figure 7:
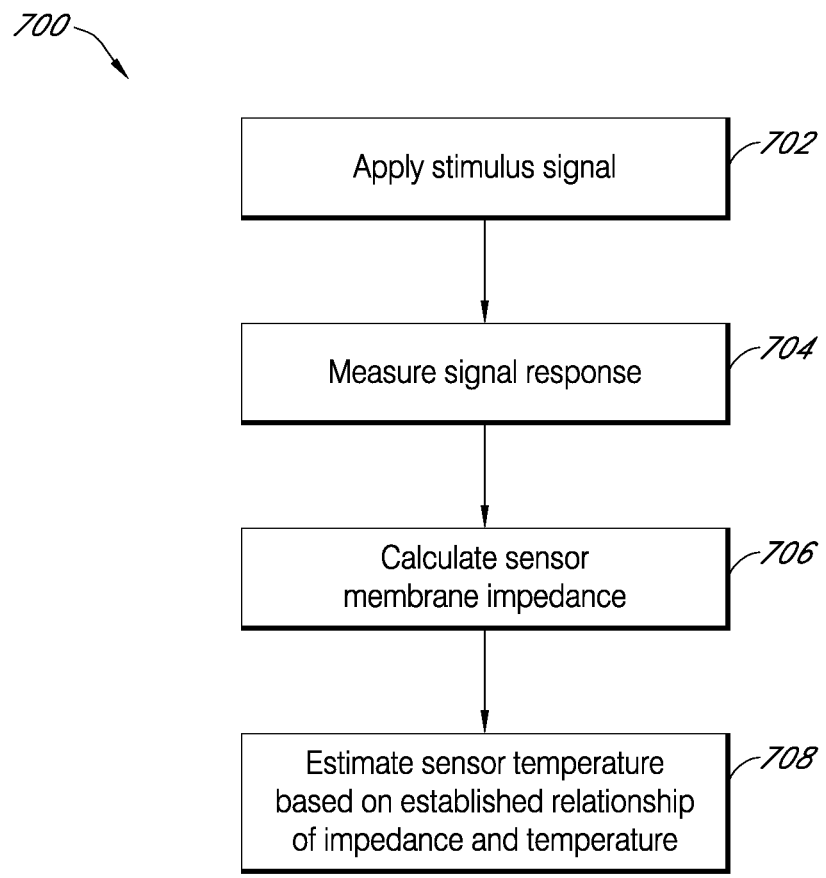
FIG. 7 is a flowchart describing a process for determining a temperature associated with a sensor by correlating an impedance measurement to a predetermined temperature-to-impedance relationship in accordance with one embodiment.

FIG. 7 is a flowchart of a process 700 for determining a sensor temperature or temperature of a sensor environment in accordance with various embodiments. At step 702, a stimulus signal can be applied to an analyte sensor, and a response can be measured and recorded at step 704. Impedance can be calculated based on the signal response at step 706. The impedance can be calculated using, for example, any of the techniques described herein, such as those described with reference to FIGS. 4-6. A temperature of the sensor can be estimated based on a predetermined relationship between impedance and temperature at step 708.

A system for measuring impedance between two electrodes can include two or more reference electrodes. With two or more reference electrodes, one reference electrode can be a primary reference electrode. The first reference electrode can contain silver/silver-chloride (Ag/AgCl), for example. The first reference electrode, that is, the reference electrode that includes Ag/AgCl, for example, can be generally stable to fluctuations in temperature. The second reference electrode can contain one or more materials that are individually or in combination less stable than an Ag/AgCl reference electrode to fluctuations in temperature.

The correlation between impedance and temperature for a particular sensor can be stored in the sensor electronics. Therefore, when the impedance of the sensor membrane is measured by, for example, any of the techniques described herein, such as those described with reference to FIGS. 2-4, the corresponding temperature of the sensor environment can be recalled from stored data in the sensor electronics. Alternatively, look-up tables correlating impedance to temperature can be used to determine the temperature corresponding to measured impedance. The sensor can display the measured impedance of the sensor membrane, for example, as an output. A user can then use this impedance value to find a corresponding temperature value on the look-up table. Moreover, the user can provide the temperature value determined by reference to the look-up table as an input to the sensor.

The temperature can be used to estimate analyte concentration values (such as, for example, glucose concentration) using sensor data or otherwise used for further processing and additionally or alternatively outputting. For example, the temperature can be used to compensate for temperature effects on various sensor properties (such as, for example, sensor sensitivity). More accurate analyte concentration values can be estimated based on the temperature compensation, and the more accurate analyte concentrations can be outputted to a display or used to trigger an alert using a glucose monitoring system.

A relationship between various sensor properties, such as sensor sensitivity, and different temperatures can be mathematically modeled (such as, for example, by fitting a mathematical curve to data using one of the modeling techniques described herein). Furthermore, the mathematical model can be used to compensate for temperature effects on the various sensor properties, such as sensor sensitivity. A sensitivity of a sensor, which can be affected by the sensor's temperature, can be determined based on associating a measured impedance of the sensor to the mathematical curve. The predetermined relationship between impedance and temperature can be determined by studying impedances of similar sensors over a range of temperatures. Sensor data can then be converted to estimated analyte concentration values based on the determined sensor sensitivity.

Analyte sensors can have an essentially linear relationship of impedance to temperature after a sensor run-in period. For example, a substantially linear relationship between impedance and temperature may be observed beginning after a period of time following sensor implantation in which the sensor can being to stabilize. The period of time in which the sensor can stabilize can last, for example, less than about one hour, for about one hour, for about two hours, for about three hours, for about four hours, for about five hours, for about twelve hours, for about twenty-four hours, or for greater than twenty-four hours. The slope of the linear relationship between impedance and temperature can be established by studying sensors made in substantially the same way as the sensor is used over a range of temperatures. In some embodiments, therefore, a sensor temperature can be estimated by measuring, for example, an impedance value of the sensor's membrane and applying the impedance value to the established linear relationship. In other embodiments, the relationship of impedance to temperature can be non-linear. In such embodiments, the non-linear relationship between impedance and temperature can be characterized using an established non-linear relationship.

A temperature compensation factor can be based, at least in part, on a temperature determined by measuring the overall capacitance between two parallel elongated conductive bodies (such as, for example, electrodes). Capacitance between two electrodes can be affected as a sensor membrane swells or contracts in response to temperature fluctuations. Capacitance can be affected as the distance between the electrodes changes, either by increasing or decreasing. For example, if the sensor membrane swells, the distance between the electrodes can increase. Likewise, if the membrane contracts in response to a temperature change, that is, as the temperature decreases, for example, the distance between the electrodes can decrease.

Capacitance between two parallel electrodes can also be affected as the dielectric strength of the insulation surrounding the electrodes changes. Accordingly, that two working electrodes can have different insulating materials. Insulating materials can include any of the insulating materials described elsewhere herein. For example, insulating materials can comprise a non-conductive polymer, such as, polyurethane or polyimide.

The correlation between capacitance measured between two parallel electrodes and temperature for a particular sensor can be stored in the sensor electronics. Therefore, when the capacitance between two parallel electrodes is measured, the corresponding temperature of the sensor environment can be recalled from stored data in the sensor electronics. Alternatively, look-up tables correlating capacitance measured between two parallel electrodes with temperature can be used to determine the temperature for a measured capacitance. For example, the sensor can display the capacitance measured between two parallel electrodes, for example, as an output. A user can then use this capacitance value to find a corresponding temperature value on the look-up table. Moreover, the user can provide the temperature value determined by reference to the look-up table as an input to the sensor.

A system for measuring temperature in a sensor environment can include measurement through bias potential. One or more semiconductors either alone or in combination with other circuit components can be operably connected to the sensor. For example, the one or more semiconductors or other circuit components can be unaffected by a normal sensor bias voltage. Accordingly, to enable the one or more semiconductors or other circuit components, the bias potential can be changed. By enabling the one or more semiconductors or other circuit components, other sensing measurements (such as, for example, temperature) can advantageously be taken without adding extra wires beneath to the system or additional electrical connections to the sensor. Temperature can therefore be determined in a manner that minimizes size, cost, and complexity.

Figure 8A:
FIG. 8A is a schematic representation of a multi-electrode analyte sensor.
Figure 8B:
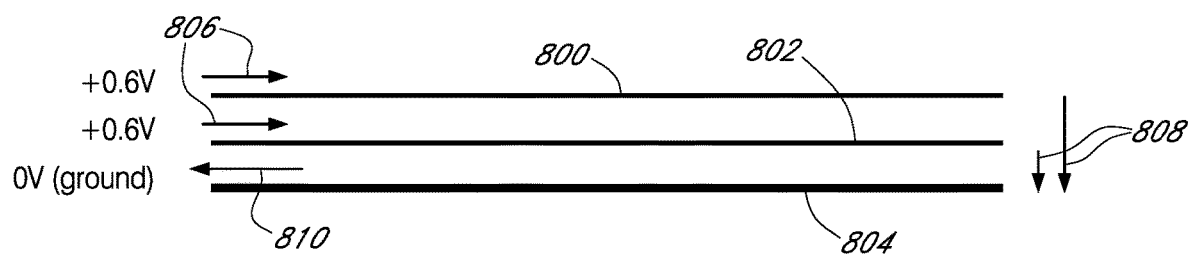
FIG. 8B is a schematic representation illustrating the current flow through the multi-electrode analyte sensor of FIG. 8A when an equal bias potential is applied to each of the two working electrodes.

With prior art analyte sensors, a potentiostat is used to measure the electrochemical reaction(s) at the electrode(s). A typical dual-electrode analyte sensor is depicted schematically in FIG. 8A. A potentiostat may apply a constant potential between the working electrode 800 and reference electrode 802 to produce a current value. The current that is produced at the working electrode (and flows through the circuitry to the counter electrode) can be proportional to the diffusional flux of $H_2O_2$. Accordingly, a raw signal may be produced that can be representative of the concentration of glucose in the host's body. For example, a voltage of about 600 mV can be applied to the working and counter electrodes 800, 802, and the reference electrode 804 can be maintained at about 0V. As shown in FIG. 8B, current flows in the direction of arrow 806 through the working and counter electrodes 800, 802. Current then flows in the direction of arrow 808 from the working and counter electrodes 800, 802 to the reference electrode 804 and through the reference electrode 804 in the direction of arrow 810 as a result of the difference in bias potential.

Additional sensing elements can be placed in series between the working and counter electrodes, including, for example, a thermistor. Accordingly, a temperature compensation factor can be based, at least in part, on a temperature determination made by a thermistor in combination with any of the additional semiconductor or other circuit components described herein.

Figure 9A:
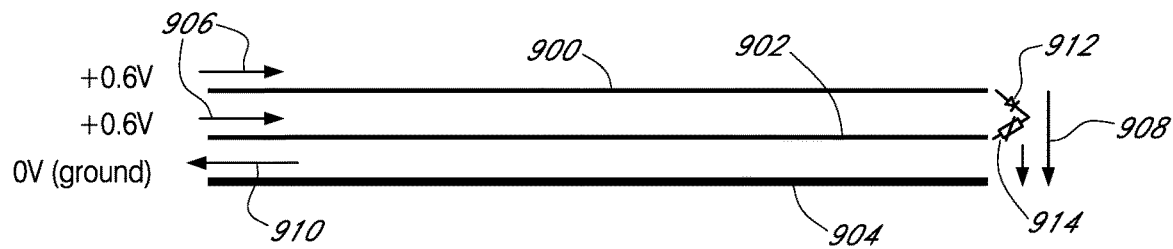
FIG. 9A is a schematic representation illustrating the current flow through the multi-electrode analyte sensor of FIGS. 8A and 8B with the addition of a diode and a thermistor connected in series between two working electrodes when an equal bias potential is applied to each of the two working electrodes.
Figure 9B:
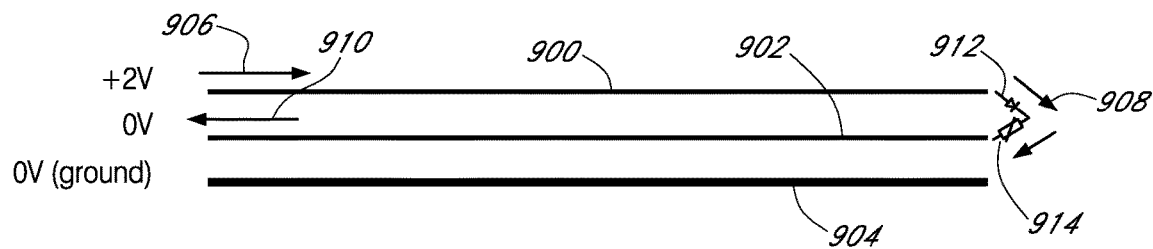
FIG. 9B is a schematic representation illustrating the current flow through the multi-electrode analyte sensor of FIG. 9A when a positive bias potential is applied to the first working electrode and the second working electrode is set to ground.

With reference to FIGS. 9A and 9B, a diode 912 and thermistor 914 can be connected in series between the working and counter electrodes 900, 902. For example, the diode 912 can be placed in series between the working electrode 900 and the thermistor 914, and the thermistor 914 can be placed in series between the diode 912 and the counter electrode 902. When the working and counter electrodes 900, 902 are maintained at substantially the same potential (such as, for example, 600 mV), current will not flow through the diode 912 or thermistor 914. When the diode is switched "off," as shown in FIG. 9A for example, current can flow through the working and counter electrodes 900, 902 in the direction of arrow 906. Current can also flow in the direction of arrow 908 from the working and counter electrodes 900, 902 to the reference electrode 904 and through the reference electrode 904 in the direction of arrow 910.

The diode 912 and thermistor 914 can be activated, for example, by changing the voltage applied to the working and counter electrodes 900, 902. As shown in FIG. 9B, the diode 914 can be switched on by altering the potential applied across the working and counter electrodes 900, 902 to induce a current therebetween. For example, a voltage of about 1V, about 1.25V, about 1.5V, about 1.75V, about 2V, about 2.25V, about 2.5V, about 2.75V, about 3V, or more than about 3V can be applied to a working electrode 900. Preferably, a voltage of about 2V can be applied to the working electrode 900. The voltage applied to the counter electrode 902 can be decreased below the normal bias value of about 600 mV. For example, a voltage of about 500 mV, about 400 mV, about 300 mV, about 200 mV, about 100 mV, or about 0V can be applied to the counter electrode 902. Preferably, a voltage of about 0V can be applied to the counter electrode 902. With continued reference to FIG. 9B, when the diode is switched to "on," for example by altering the voltages applied to the working and counter electrodes 900, 902, current can flow through the working electrode 900 in the direction of arrow 906. Current can then flow from the working electrode 900 to the counter electrode 902, including through the diode 912 and through the thermistor 914 in the direction of arrow 908. Current can then flow through the counter electrode 902 in the direction of arrow 910. Accordingly, a temperature of the sensor environment can be determined by inducing current flow through the thermistor 914.

Figure 10A:
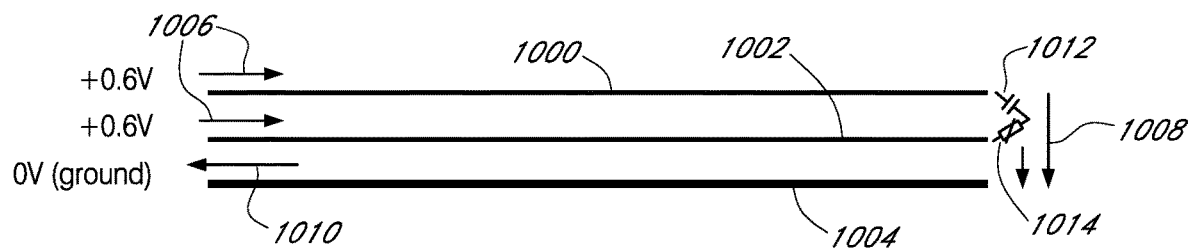
FIG. 10A is a schematic representation illustrating the current flow through the multi-electrode analyte sensor of FIGS. 8A and 8B with the addition of a capacitor and a thermistor connected in series between two working electrodes when an equal bias potential is applied to each of the two working electrodes.
Figure 10B:
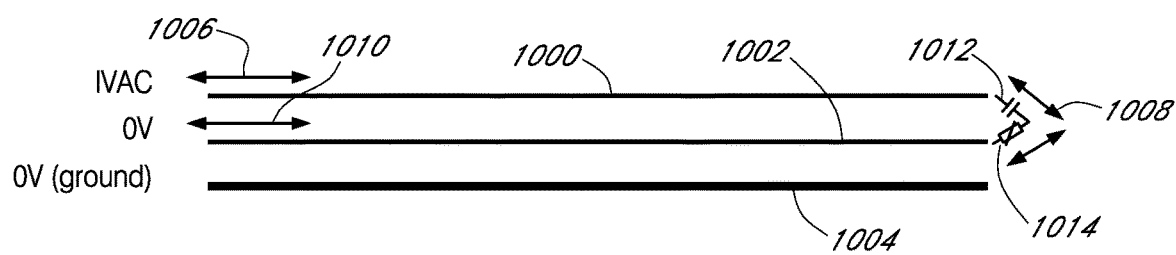
FIG. 10B is a schematic representation illustrating the current flow through the multi-electrode analyte sensor of FIG. 10A when an AC bias potential is applied to the first working electrode and the second working electrode is set to ground.

A capacitor 1012 and thermistor 1014 can be placed in series between the working and counter electrodes 1000, 1002. As shown in FIGS. 10A and 10B, the capacitor 1012 can be placed in series between a working electrode 1000 and a thermistor 1014, and the thermistor 1014 can be placed in series between the capacitor 1012 and a counter electrode 1002. When the working and counter electrodes 1000, 1002 are biased to a substantially equal DC voltage (such as, for example, about 600 mV), the sensor system functions as normal and will not affected by the additional circuit components. As shown in FIG. 10A, for example, when the working and counter electrodes 1000, 1002 are both biased to about 600 mV, current can flow through the working and counter electrodes 1000, 1002 in the direction of arrow 1006. Current can then flow from the working and counter electrodes 1000, 1002 to the reference electrode 1004 in the direction of arrow 1008, and through the reference electrode 1004 in the direction of arrow 1010.

To activate the capacitor 1012 and the thermistor 1014, a voltage pulse can be applied to the working electrode 1000 while the counter electrode 1002 can be maintained at a different, constant bias voltage. For example, a pulsed voltage of about 1V, about 1.25V, about 1.5V, about 1.75V, about 2V, about 2.25V, about 2.5V, about 2.75V, about 3V, or more than about 3V can be applied to the working electrode 1000. The voltage applied to the counter electrode 1002 can be, for example, about 500 mV, about 400 mV, about 300 mV, about 200 mV, about 100 mV, or about 0V.

As shown in FIG. 10B, a current can be induced through the thermistor 1014 by applying an alternating current ("AC") voltage to the working electrode 1000 while a bias voltage of about 0V is applied to the counter electrode 1002. For example, an AC voltage of about 0.1V AC, about 0.25V AC, about 0.5V AC, about 0.75V AC, about 1V AC, about 1.25V AC, about 1.5V AC, about 1.75V AC, or about 2V AC can be applied to the working electrode 1000. Preferably, as shown in FIG. 10B, a voltage of about 1V AC can be applied to the working electrode 1000 while the counter electrode 1002 can be maintained at about 0V. Accordingly, current can flow through the working electrode 1000 in the direction of arrow 1006. As the capacitor 1012 is either charged or discharged, current can flow through the thermistor 1014 in the direction of arrow 1008 and through the counter electrode 1002 in the direction of arrow 1010. Accordingly, a temperature of the sensor environment can be determined by inducing current flow through the thermistor 1014.

Figure 11:
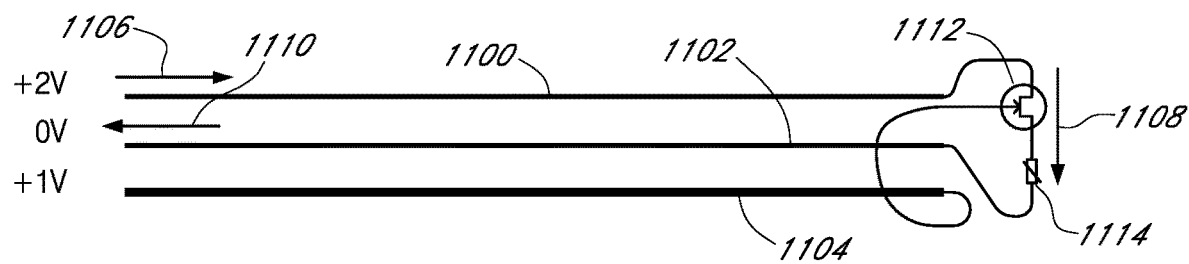
FIG. 11 is a schematic representation illustrating the current flow through the multi-electrode analyte sensors of FIGS. 8A and 8B with the addition of a field effect transistor connected at its source to the first working electrode, at its drain to the second working electrode, and at its gate to the reference electrode when a positive bias potential is applied to the first working electrode, a relatively smaller positive bias potential is applied to the reference electrode, and the second working electrode is set to ground.

A field effect transistor ("FET") 1112 can be used to activate a thermistor 1114 operably connected to an analyte sensor. For example, an FET 1112 can be placed in the system by connecting the source to a working electrode 1100 and connecting the gate to a reference electrode 1104. As shown in FIG. 11, a thermistor 1114 can be placed in series between the drain of the FET 1112 and a counter electrode 1102. When the reference electrode 1104, and thus the gate of the FET 1112, is at about 0V, for example, the FET 1112 can be "off" such that current will not flow through the thermistor 1114 and the sensor system can function normally.

Temperature of the sensor environment can be measured by turning the FET 1112 gate "on." The FET 1112 can be switched "on," as shown in FIG. 11 by applying a potential across the FET 1112 from its source to its drain. When a potential is maintained across the FET 1112 from its source to its drain, current can flow across the FET 1112 and thus through the thermistor 1114. A potential can be applied across the FET 1112 from its source to its drain, for example, by applying a different voltage to the working electrode 1100 than a voltage applied to the counter electrode 1102. As shown in FIG. 11, for example, a voltage of about 2V can be applied to the working electrode 1100, a voltage of about 1V can be applied to the reference electrode 1104, and the counter electrode 1102 can be maintained at a voltage of about 0V. Accordingly, current can flow through the working electrode 1100 in the direction of arrow 1106, from the source of the FET 1112 to its drain in the direction of arrow 1108. Current can therefore flow through the thermistor 1114 in the direction of arrow 1108. A temperature of the sensor environment can therefore be determined.

The additional sensor components, such as those described above and including, for example, a diode, capacitor, or FET, can be utilized in a sensor system substantially as described above but without the addition of a thermistor. When the thermistor is removed from the circuits as described above, simple diagnostic tests of the sensor can be performed. For example, the additional sensor components (such as, for example, diode, capacitor, or FET) can be activated to detect the presence of a broken wire in the system.

Moreover, an electrochemical sensor can be added in series with the additional sensor components (such as, for example, diode, capacitor, or FET) in place of or in addition to the thermistor. When an additional electrochemical sensor is placed in series with the other sensor components as described above, additional analyte measurements can be taken when the circuit is activated. The additional analyte measurement can be of a different analyte species than is being monitored by the main sensor system. Additional analyte measurements can be taken less frequently as the main analyte measurement. For example, an additional analyte measurement can be taken once every two times, once every three times, once every four times, once every five times, or less frequently that once every five times that the main analyte value is measured. Alternatively, the additional analyte measurement can be taken more frequently than the main analyte measurement. For example, additional analyte measurements can be taken twice as often, three times as often, four times as often, five times as often, or more than five times as often as the main analyte measurement. The additional analyte measurement can be taken as often as the main analyte measurement. Furthermore, neither the main analyte measurement nor the additional analyte measurement need be taken at regularly spaced intervals. That is, either one or both of the main analyte measurement or the additional analyte measurement can be taken at irregularly spaced intervals.

The additional electrochemical sensor can measure the same analyte as the analyte species being measured by the main sensor system. Accordingly, the additional analyte measurement can be used in conjunction with measurement of the main sensor to ensure accuracy of the sensor system. In other words, the additional electrochemical sensor can function as a redundant sensor. Redundant analyte a redundant analyte measurement can be taken once every two times, once every three times, once every four times, once every five times, or less frequently that once every five times that the main analyte value is measured. Alternatively, the redundant analyte measurement can be taken more frequently than the main analyte measurement. For example, redundant analyte measurements can be taken twice as often, three times as often, four times as often, five times as often, or more than five times as often as the main analyte measurement. The redundant analyte measurement can be taken as often as the main analyte measurement. Furthermore, neither the main analyte measurement nor the redundant analyte measurement need be taken at regularly spaced intervals. That is, either one or both of the main analyte measurement or the redundant analyte measurement can be taken at irregularly spaced intervals.

In one embodiment with at least two electrodes, one electrode (such as, for example, the working electrode) has a constant bias potential and a second electrode (such as, for example, another working electrode, the reference electrode, or the counter electrode) has a changing bias potential. The first electrode is designed to measure analyte (e.g., glucose) concentration. By changing the bias potential of a second electrode, different parameters (such as, for example, temperature) can be measured. In another embodiment, the sensor system comprises a single working electrode. When powered at its normal bias potential, the working electrode is in a mode for glucose measurement. With this embodiment, at certain times, the bias potential may be changed. For example, the bias potential may be decreased to a level such that the working electrode can no longer oxidize the measured species (e.g., hydrogen peroxide) that is indicative of glucose concentration. Nonetheless, at a lower bias potential, the working electrode may be capable of measuring some other parameter that is indicative of temperature or temperature change. With this embodiment, the working electrode's bias potential may alternate from one bias potential (for measuring glucose) to another bias potential (for measuring another parameter, such as temperature or temperature change). The timing and frequency of the changes in applied bias potential may be dependent on certain parameters that are indicative of a possible temperature change. For example, if the system detects a high rate of temperature change, the system may be configured to apply the bias potential used to measure temperature change.

In another embodiment, the sensor system comprises at least two working electrodes that are substantially identical: a first and second working electrode. During use, in one mode, both working electrodes may be at a bias potential set for measuring glucose. In another mode, the second working electrode may remain at the above-described bias potential and set for measuring glucose, while the first working electrode may be temporarily powered down. After a predetermined time period, when power is re-applied to the first electrode, its transient response (i.e., the time it takes to recover to its normal signal level, as indicated by the second working electrode) can be observed to infer certain information, such as temperature or temperature changes. With this two electrode system, unlike the one electrode system, the system is capable of continuing taking continuous glucose readings with the electrode that was not powered down. In addition, the electrode that is not powered down provides a basis for the electrode that was powered down (and then reactivated) to compare to, and thereby gather information (e.g., temperature information). Thus, with the two electrode system, the two electrode configuration allows the system to differentiate the transient response of the powered down electrode from actual changes in glucose level.

A temperature determination can be made less frequently than an analyte measurement is taken. For example, a temperature determination can be made once every two times, once every three times, once every four times, once every five times, or less frequently that once every five times that the analyte value is measured. Alternatively, the temperature determination can be made more frequently than the analyte measurement is taken. For example, the temperature determination can be made twice as often, three times as often, four times as often, five times as often, or more than five times as often as the analyte measurement is taken. The temperature determination can be made as often as the analyte measurement is taken. Furthermore, subsequent temperature determinations need not be made at regularly spaced intervals. That is, temperature determinations can be made at irregularly spaced intervals.

A first temperature determination can be made and a second temperature determination can be made. The first and second temperature determinations can be made independently of one another according to any of the methods disclosed herein for determining temperature of a sensor environment. For example, the first temperature can be determined by use of a core sensor that functions as a thermocouple, and a second temperature can be determined by any one of measurement of force deflection of a shape memory material included in the sensor, use of fiber optics, calculation of sensor impedance, measurement of capacitance between two electrodes, or measurement through a thermistor operably connected to any one or more of a diode, a capacitor, or an FET. Alternatively, the first temperature can be determined by of measurement of force deflection of a shape memory material included in the sensor, and a second temperature can be determined by any one of use of a core sensor that functions as a thermocouple, use of fiber optics, calculation of sensor impedance, measurement of capacitance between two electrodes, or measurement through a thermistor operably connected to any one or more of a diode, a capacitor, or an FET. Additionally, the first temperature can be determined by use of fiber optics, and a second temperature can be determined by any one of use of a core sensor that functions as a thermocouple, measurement of force deflection of a shape memory material included in the sensor, calculation of sensor impedance, measurement of capacitance between two electrodes, or measurement through a thermistor operably connected to any one or more of a diode, a capacitor, or an FET. Moreover, the first temperature can be determined by calculation of sensor impedance, and a second temperature can be determined by any one of use of a core sensor that functions as a thermocouple, measurement of force deflection of a shape memory material included in the sensor, use of fiber optics, measurement of capacitance between two electrodes, or measurement through a thermistor operably connected to any one or more of a diode, a capacitor, or an FET. Also, the first temperature can be determined by measurement of capacitance between two electrodes, and a second temperature can be determined by any one of use of a core sensor that functions as a thermocouple, measurement of force deflection of a shape memory material included in the sensor, use of fiber optics, calculation of sensor impedance, or measurement through a thermistor operably connected to any one or more of a diode, a capacitor, or an FET. Furthermore, the first temperature can be determined by measurement through a thermistor operably connected to any one or more of a diode, a capacitor, or an FET, and a second temperature can be determined by any one of use of a core sensor that functions as a thermocouple, measurement of force deflection of a shape memory material included in the sensor, use of fiber optics, calculation of sensor impedance, or measurement of capacitance between two electrodes.

A first temperature determination can be taken less frequently as a second temperature determination. For example, a first temperature determination can be made once every two times, once every three times, once every four times, once every five times, or less frequently that once every five times that the second temperature determination is made. Alternatively, the first temperature determination can be made more frequently than the second temperature determination is made. For example, a first temperature determination can be made twice as often, three times as often, four times as often, five times as often, or more than five times as often as the second temperature determination. The first temperature determination can be made as often as the second temperature determination is made. Furthermore, neither the first temperature determination nor the second temperature determination need be made at regularly spaced intervals. That is, either one or both of the first or second temperature determinations can be made at irregularly spaced intervals.

Any additional methods of measuring temperature known to those of skill in the art can likewise be used to make a first, a second, or any additional temperature determinations. A first, a second, or any subsequent temperature determinations may be made by use of the same method. Use of different methods to determine temperature may also be used to make a first, a second, or any subsequent temperature determinations. A first, a second, or any subsequent temperature determinations may be made independently of any other temperature determinations.

Two or more temperature determinations can be compared. For example, a first temperature determination can be compared to a second determination. The first and second temperature determinations may have been made independently of one another. Comparison of two or more temperature determinations can provide for verification of the temperature of the sensor environment. The temperature of the sensor environment can be verified for example, when a first temperature determination and a second temperature determination are substantially equal. That is, the temperature of the sensor environment can be verified, for example, when the difference between the first temperature determination and the second temperature determination is less than about 5° C., less than about 4° C., less than about 3° C., less than about 2° C., less than about 1.5° C., less than about 1.25° C., less than about 1.1° C. less than about 1° C., less than about 0.75° C., less than about 0.5° C., less than about 0.25° C., or less than about 0.1° C. When temperature verification has been provided, any one of the two or more temperature determinations can be used to calculate a temperature compensation factor according to any of the methods disclosed herein. For example, if comparison between a first temperature determination and a second temperature determination has provided verification of the temperature of the sensor environment, either the first temperature determination or the second temperature determination can be used to calculate a temperature compensation factor according to any of the methods disclosed herein.

An average of two or more temperature determinations can be taken. For example, an average of the first temperature determination and the second temperature determination can be taken if the difference between the first and second temperature determinations is from about 0.1° C. to about 5° C., from about 0.1° C. to about 4° C., from about 0.1° C. to about 3° C., from about 0.1° C. to about 2° C., from about 0.1° C. to about 1.5° C., from about 0.1° C. to about 1° C., from about 0.25° C. to about 5° C., from about 0.5° C. to about 5° C., from about 0.75° C. to about 5° C., from about 1° C. to about 5° C., from about 1.5° C. to about 5° C., from about 2° C. to about 5° C., from about 3° C. to about 5° C., from about 4° C. to about 5° C., from about 0.25° C. to about 4° C., from about 0.5° C. to about 3° C., from about 0.75° C. to about 2° C., or from about 1° C. to about 1.5° C. The average between two or more temperature determinations can be used to calculate a temperature compensation factor according to any of the methods disclosed herein. Calculation of an average temperature can provide for a more accurate determination of a temperature compensation factor, for example, if any one of the two or more temperature determinations does not accurately reflect the true temperature of the sensor environment.

Processing Temperature Information

To determine a temperature compensation factor for use with a continuous analyte sensor, a temperature of the sensor environment can first be determined, as discussed above. Once the temperature, or change in temperature from a previous measurement, of the sensor environment has been determined, the measured temperature can be processed in order to determine a temperature compensation factor or value.

A priori information can be used to compensate for temperature changes. Such a priori information may be stored in the sensor so that when a temperature measurement is taken, the temperature value can be compared to stored temperature values. When a stored temperature value has been matched to the measured temperature value, a stored compensation factor corresponding to the stored temperature value can be applied to the measured sensor signal to determine an analyte concentration. The stored compensation value can be applied to the measured sensor signal until a subsequent measured temperature value differs from a previous measured temperature value. Thus, the subsequently measured temperature value may correspond to a different stored temperature value, which may have a different stored compensation factor corresponding therewith. Accordingly, by comparing measured temperature values to stored temperature values and stored temperature compensation factors, a more accurate analyte concentration may be determined.

For example, based on a measured temperature value, a corresponding stored temperature compensation factor or value of a may be recalled from sensor memory. The temperature compensation factor of a can be applied to the measured sensor signal. Therefore, if an analyte concentration determined from a measured sensor signal is calculated as q mg/dl, the stored temperature compensation factor of a can be applied to the analyte concentration to report a more accurate reading to the user. That is, the sensor can report an analyte concentration of (a*q) mg/dl.

Figure 12:
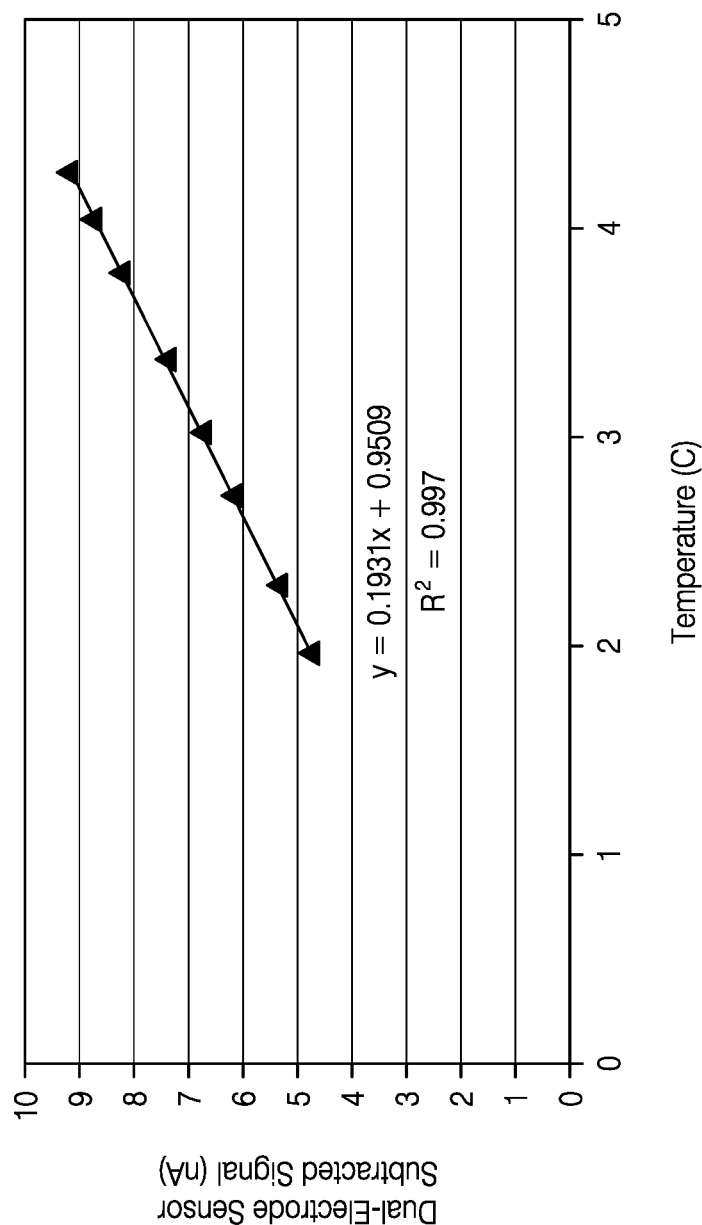
FIG. 12 is a plot illustrating the linear relationship between sensor sensitivity and sensor temperature.

Analyte sensor sensitivity is dependent, in part, upon the temperature of the sensor environment. As shown in FIG. 12, the temperature dependence of a single analyte sensor can be linear. Specifically, as temperature increases, so does the detected signal. In certain embodiments, compensation for changes in temperature can therefore be determined by comparing a measured temperature to a corresponding stored sensor sensitivity value.

Without wishing to be bound by theory, it is believed that sensor sensitivity may be a composite property of the sensor and may include, for example, temperature dependent factors such as the effect of glucose oxidase activity and membrane permeability to glucose, hydrogen peroxide, and hydrogen ions. Other elements of sensor sensitivity, such as reference capacity, glucose oxidase loading, and degree of cross-linking may be independent of temperature, but nonetheless contribute to defining inherent sensitivity. Accordingly, such factors can lead to different membrane properties and can result in different temperature compensation factors.

Figure 13:
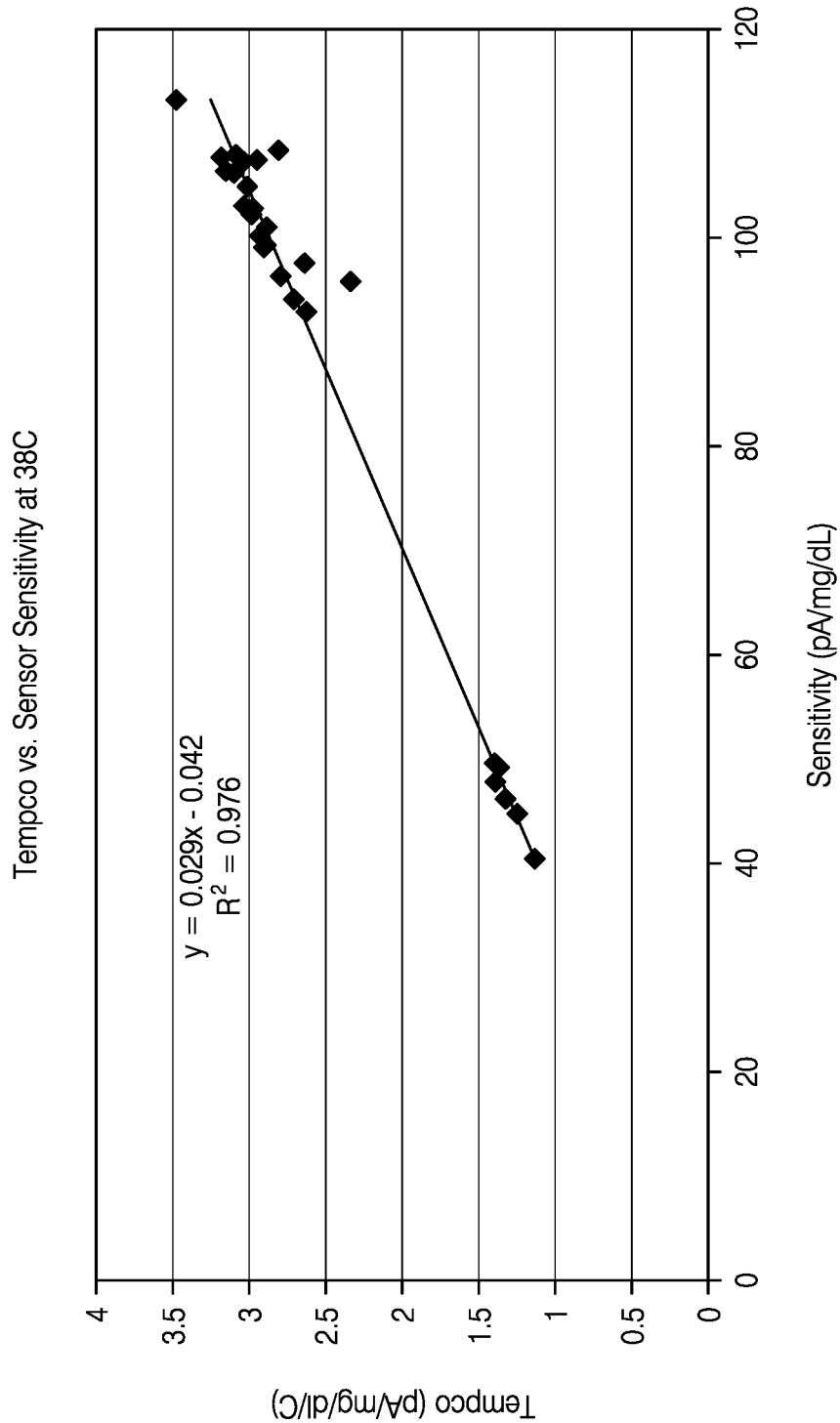
FIG. 13 is a plot illustrating the relationship between the tempco and sensitivity for various sensors measured at 38° C.

It may be difficult, therefore, to apply a universal temperature compensation factor to all sensors, because the slope of the temperature-dependent equation shown in FIG. 12, and referred to herein as the "tempco," may itself be dependent on the inherent sensitivity of a sensor. The tempco therefore represents the change in sensor sensitivity per degree C. and is dependent on the inherent sensor sensitivity, as represented in FIG. 13. However, because the sensor sensitivity changes with temperature, the equation to determine the tempco, as represented by FIG. 13, is dependent on the calibration temperature. FIG. 13, for example, is a production of this relationship for the sensor sensitivity at 38° C. If a given sensor were calibrated at a temperature other than 38° C., a different tempco vs. sensitivity relationship will need to be generated in order to determine the tempco for that sensor.

Figure 14:
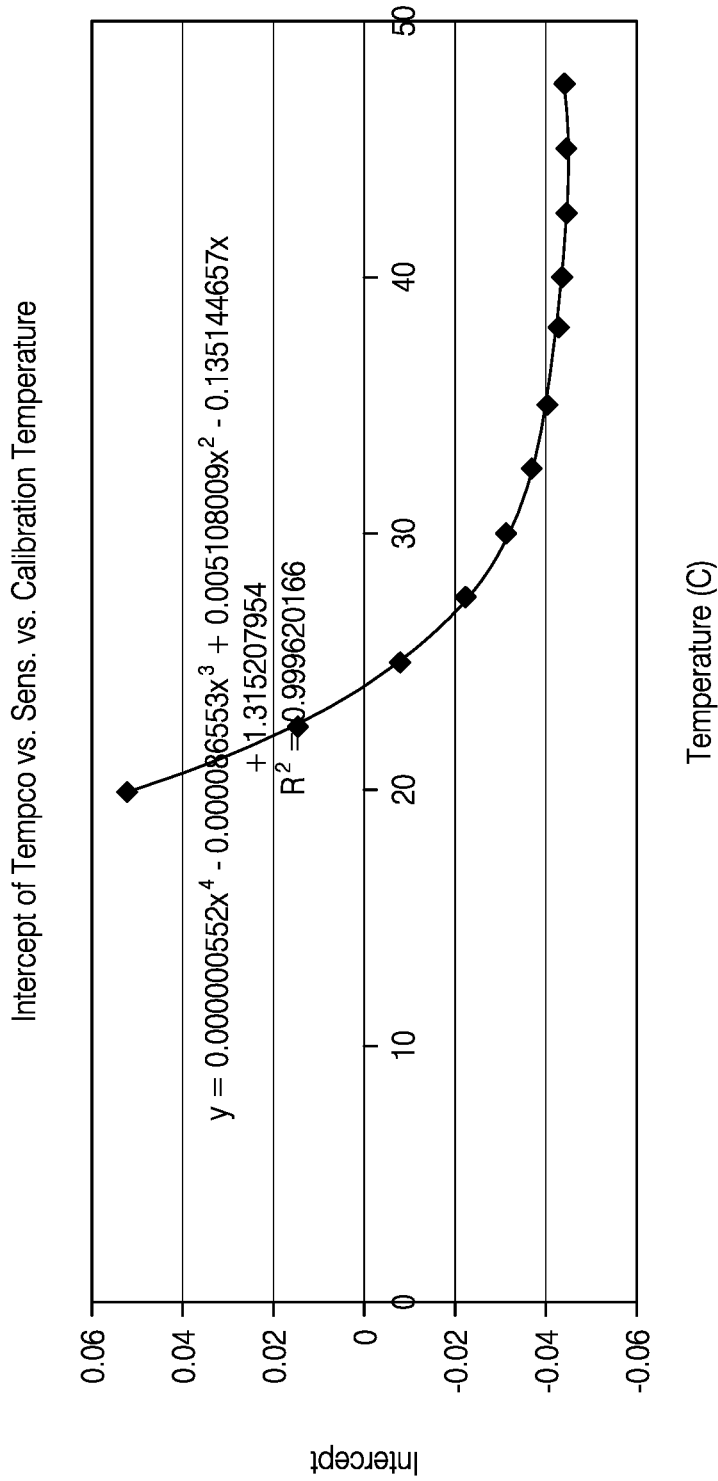
FIG. 14 is a plot illustrating the relationship between the tempco intercept and sensor calibration temperature.
Figure 15:
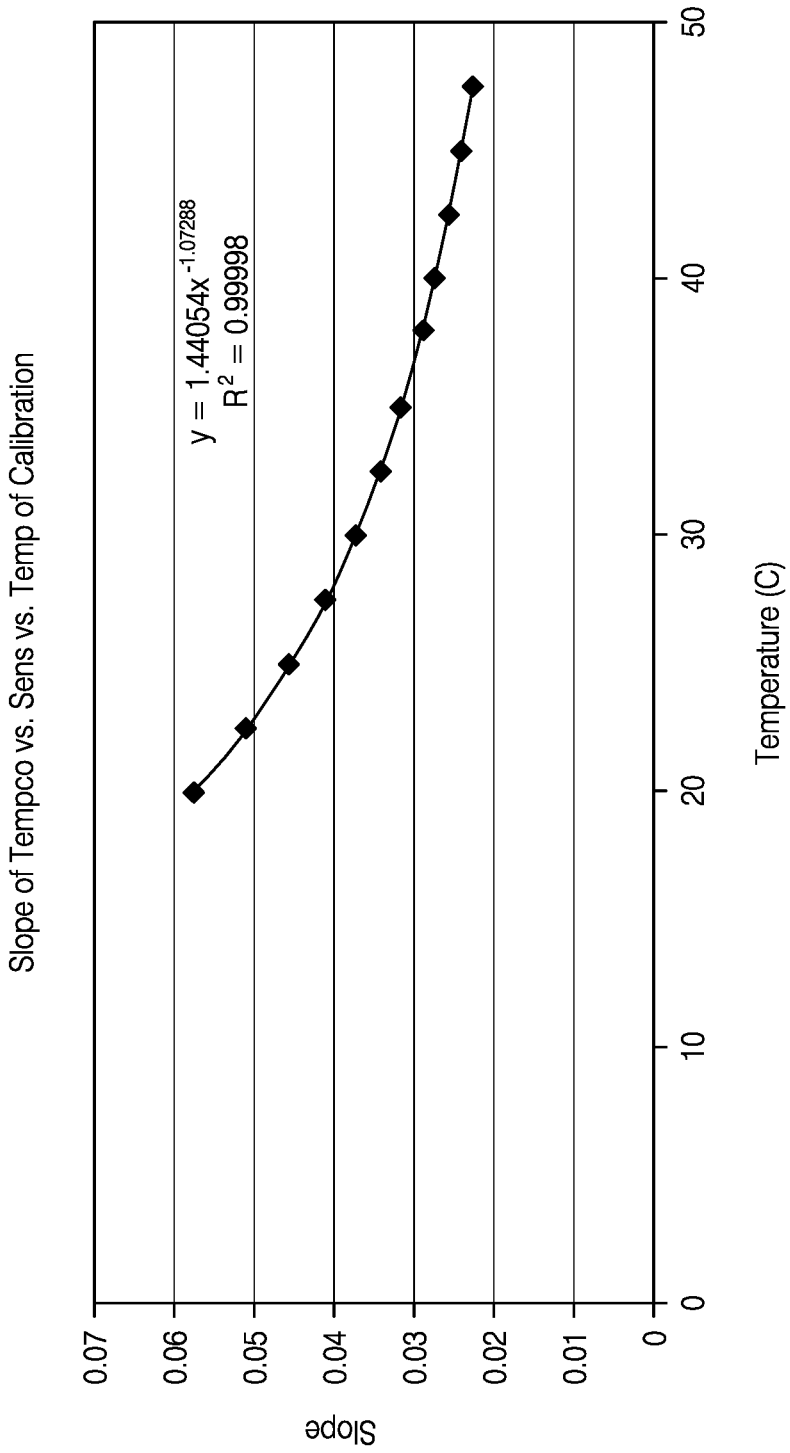
FIG. 15 is a plot illustrating the relationship between the tempco slope and sensor calibration temperature.

Accordingly, the relationship between the slope and intercept of the relationship shown in FIG. 12 can be reproduced at any temperature. For example, FIGS. 14 and 15 represent the relationships between temperature and the intercept of the tempco vs. sensor sensitivity plot for a given temperature and the slope of the tempco vs. sensor sensitivity plot for a given temperature. The relationship shown in FIG. 12 can therefore be reproduced by inputting a temperature into the equations from FIGS. 14 and 15.

In vivo, this relationship can be determined during a self-calibration cycle where both the temperature and sensitivity are known. For example, temperature can be determined by measuring temperature in accordance with any of the methods discussed above. The sensor-dependent tempco for that particular time (that is, the time of temperature measurement) can be determined by calculation or with reference to stored data. Further, as the sensitivity of a particular sensor changes over time in response to a variety of elements, the tempco of the sensor can be updated with multiple calibration points to maintain accurate temperature compensation regardless of the sensitivity of the sensor.

In certain embodiments, determining a temperature compensation factor can be based at least in part on a predictive sensitivity model. For example, tempco may be calculated using a measured temperature, and sensitivity may be predicted through other means.

Use of a calculated tempco has been shown to provide increased accuracy and precision of analyte measurements because the application of a temperature compensation factor is not dependent on a universal constant that may not suit an individual sensor at any particular point during the life of that sensor. Rather than using a constant tempco for all sensors, various embodiments provide for use of a dynamic method of determining the tempco for each sensor at each calibration point, wherein tempco is dependent on the sensitivity of the sensor during the period between reference points. Accordingly, sensor sensitivity can be determined for a particular sensor at a measured temperature, and a priori data can be used to predict a tempco for that particular sensor.

Figure 16:
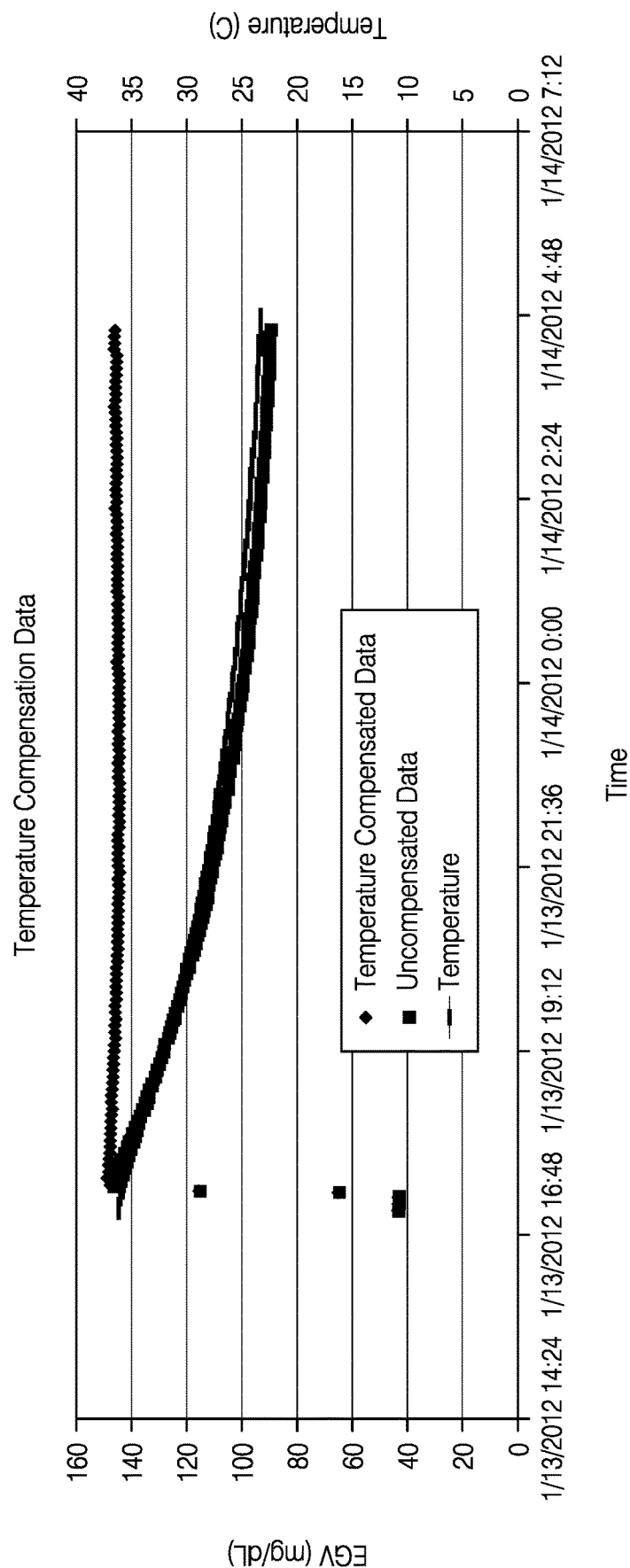
FIG. 16 is a plot of uncompensated temperature data taken over time from a sample having a constant glucose concentration as temperature of the sample decreases and of compensated temperature data over the same time period and for the same sample.

With reference to FIG. 16, advantages of applying a temperature compensation factor are shown. As illustrated, measurements of glucose concentration from an in vitro sample having a known, constant value are taken over time as the temperature of the sample (that is, the sensor environment) decreases from approximately 37° C. to approximately 22° C. As shown in FIG. 16, uncompensated measurement data decreases over time in conjunction with the decrease in temperature, regardless of the fact that the glucose concentration of the sample is a known constant. By applying a temperature compensation factor to the data to account for the decrease in temperature of the sample (that is, the sensor environment), a more accurate glucose concentration can be reported.

EXAMPLE 1

Effect of Temperature

Figure 17:
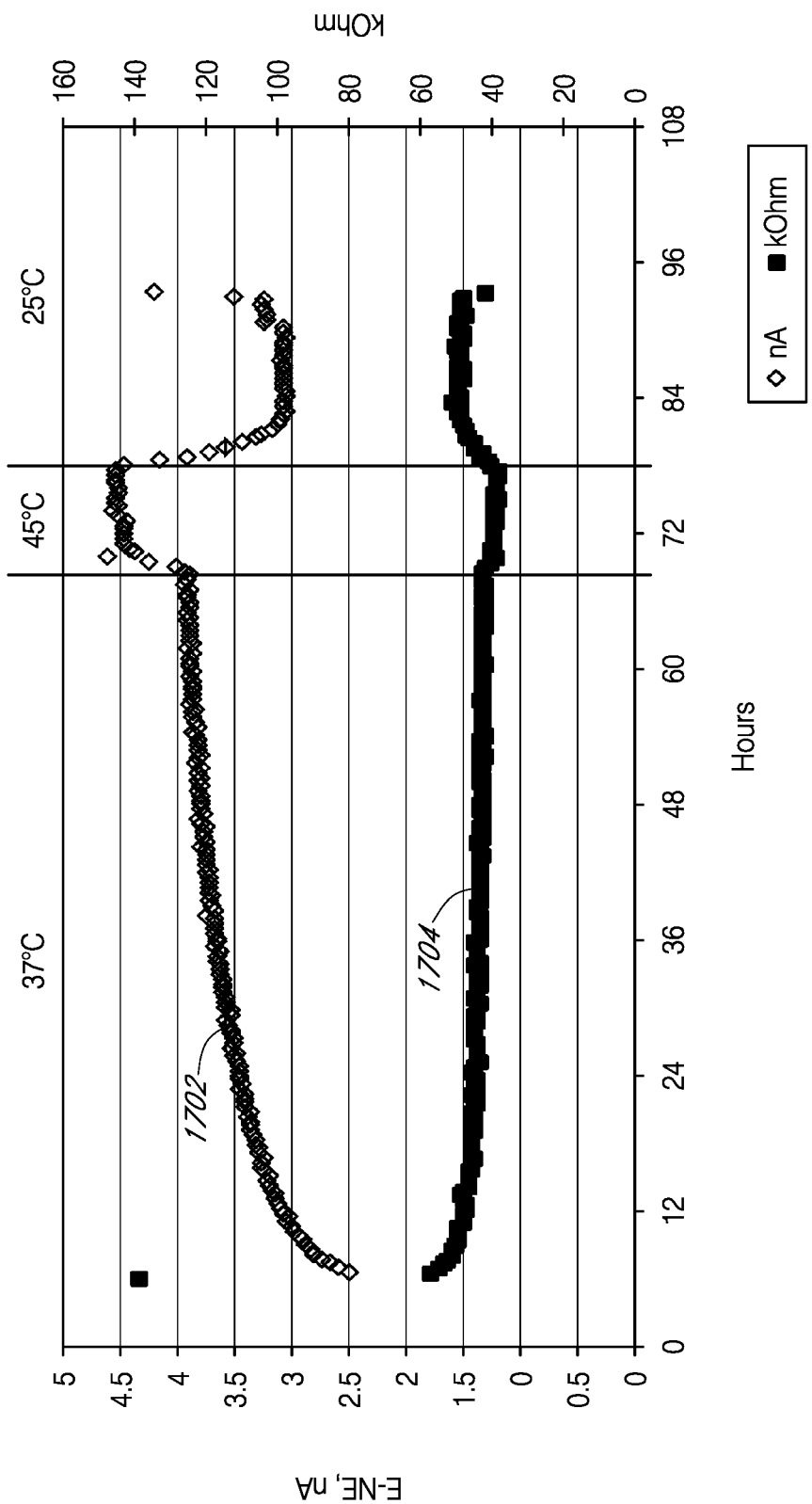
FIGS. 17-19 collectively illustrate results of studies using stimulus signals to determine sensor properties.

FIG. 17 illustrates effects of temperature on impedance and sensitivity of a sensor. Points 1702 are sensitivity values of a sensor measured over a three day time period and points 1704 are impedance values of the sensor measured over the same time period. In Example 1, the sensor is a transcutaneous-type of sensor. The temperature was initially set and maintained at 37° C., then raised to 45° C., and finally lowered to 25° C., as indicated in FIG. 17.

As illustrated in FIG. 17, both sensitivity and impedance of the sensor appear to have an inversely proportional relationship with changes in temperature.

Figure 18:
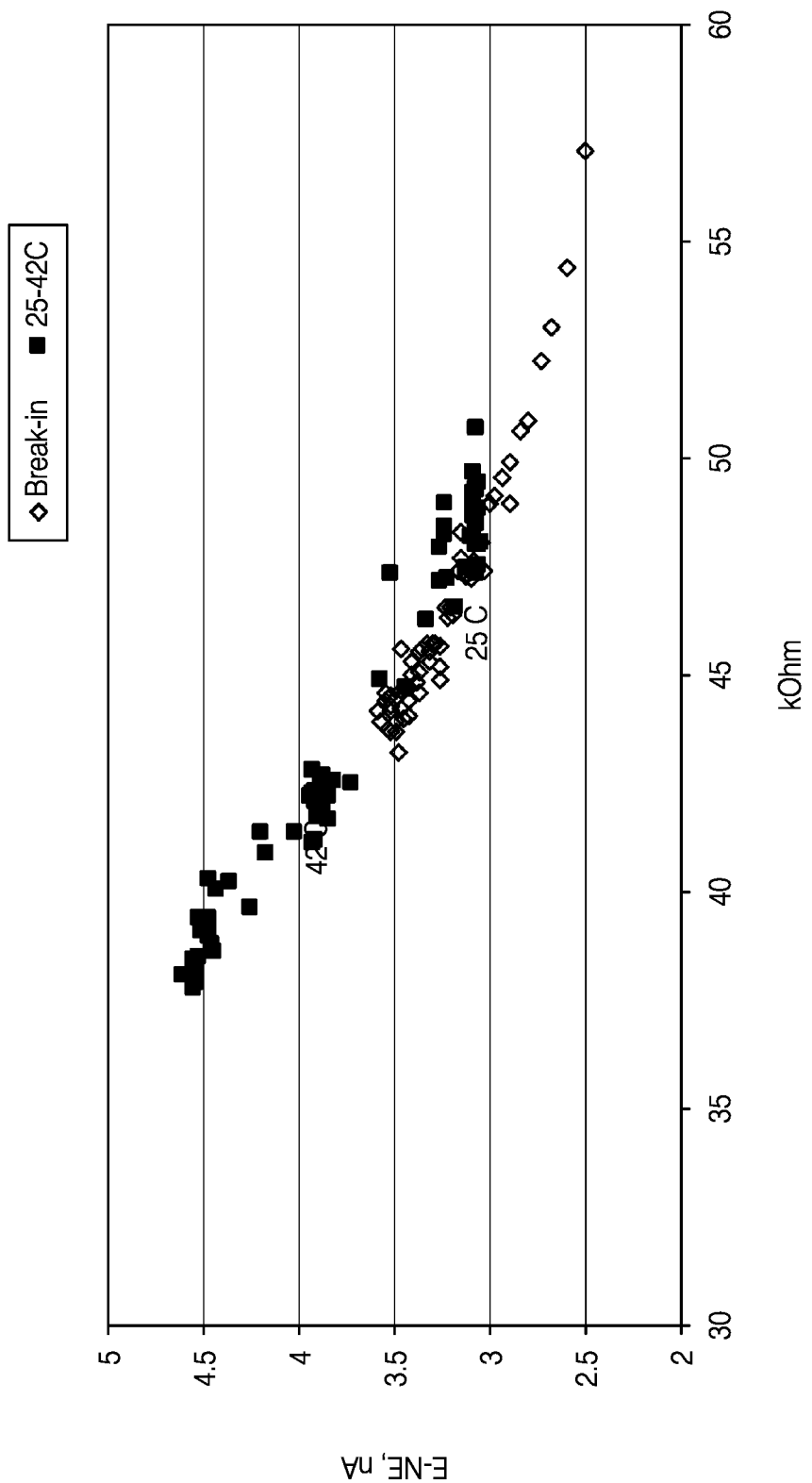

FIG. 18 is a plot of the sensitivity measurement values versus the impedance measurement values of FIG. 17. FIG. 18 illustrates points measured during sensor run-in as diamonds and points measured after run-in as squares.

EXAMPLE 2

Temperature Compensation

Figure 19:
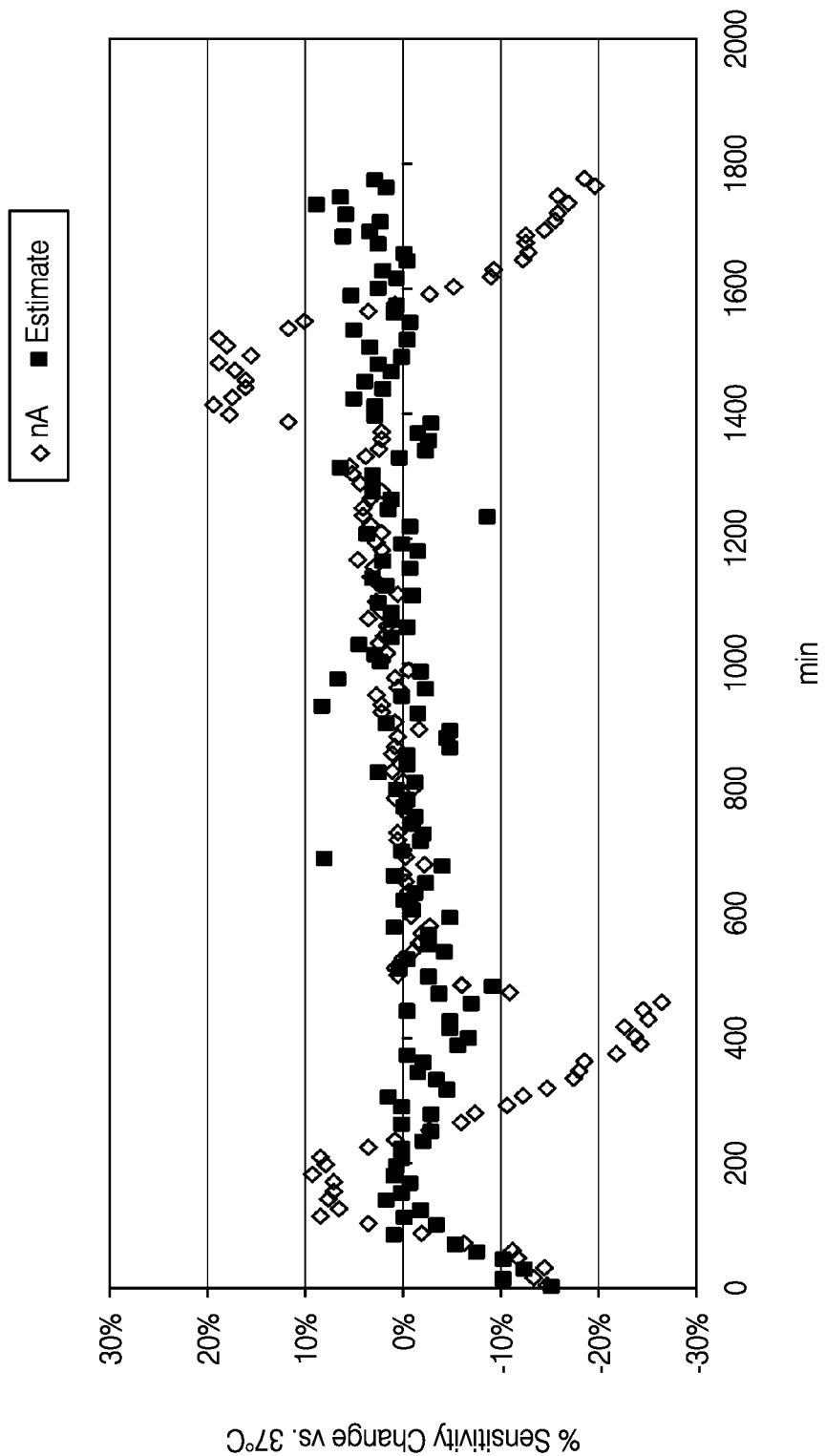

FIG. 19 illustrates compensating analyte concentration data measured by the sensor of Example 1 for effects of temperature after sensor run-in. Here, a relationship between impedance and temperature was used to compensate the sensor data. In this example, the relationship was based on an estimative curve derived from the data of FIG. 18.

The relationship between sensor sensitivity and different temperatures can then be mathematically modeled (such as, for example, by fitting a mathematical curve to data), and the mathematical model can then be used to compensate for temperature effects on the sensor sensitivity. That is, a sensitivity of a sensor (which is affected by the sensor's temperature) can be determined based on a measured impedance of the sensor applied to the mathematical curve. Sensor data can then be converted to estimated glucose values based on the determined sensor sensitivity.

Further to FIG. 19, the Mean Absolute Relative Difference (MARD) of the uncompensated data was calculated as 9.3% and the MARD of the compensated data was calculated as 2.8%.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A device for continuous in vivo measurement of glucose concentrations in a host, comprising:
   a first electrode;
   a second electrode;
   a first membrane located over at least a portion of the first electrode, the first membrane comprising an enzyme configured to catalyze a reaction of glucose and oxygen from a biological fluid in contact with the first membrane in vivo, the first membrane having a first temperature coefficient;
   a second membrane located over at least a portion of the second electrode, the second membrane having a second temperature coefficient different than the first temperature coefficient; and
   electronic circuitry operatively connected to the first electrode and to the second electrode, the electronic circuitry being configured to generate a signal representative of a concentration of glucose in the host and configured to measure at least one of an in vivo temperature or a change in temperature in vivo, the measuring using the first membrane and the second membrane.

2. The device of claim 1, wherein the first membrane and the second membrane each have a different composition.

3. The device of claim 1, wherein the first membrane and the second membrane are each configured to exhibit a different change in dimension in response to a change in temperature in vivo.

4. The device of claim 1, wherein the first membrane and the second membrane are each configured to exhibit a different change in electrical conductivity in response to a change in temperature in vivo.

5. The device of claim 1, the electronic circuitry being further configured to apply at least one potential to at least one of the first electrode or the second electrode.

6. The device of claim 5, wherein the at least one potential includes a first potential that is applied to the first electrode and a second potential that is applied to the second electrode.

7. The device of claim 6, wherein the first potential is different from the second potential.

8. The device of claim 5, further comprising a connector configured to connect the first electrode and the second electrode, wherein the connector comprises a thermistor.

9. The device of claim 8, wherein the connector further comprises a diode.

10. The device of claim 8, wherein the connector further comprises a capacitor.

11. The device of claim 5, further comprising a third electrode, wherein the first electrode and the second electrode are each working electrodes and the third electrode is a reference electrode.

12. The device of claim 11, further comprising a connector configured to connect the first electrode, the second electrode, and the third electrode, wherein the connector comprises a thermistor and a transistor.

13. The device of claim 1, wherein the electronic circuitry is configured to measure a stimulus signal passed across the first electrode and the second electrode.

14. The device of claim 13, wherein the stimulus signal is an impedance measurement.

15. The device of claim 1, further comprising a first reference electrode or a first counter electrode, and a second reference electrode or a second counter electrode, wherein the electronic circuitry is configured to measure a stimulus signal passed between the first electrode and the second electrode.

16. The device of claim 1, wherein the device is configured to apply a first bias potential to the first electrode and a second bias potential to the second electrode, wherein the second bias potential varies over time, and wherein the electronic circuitry is configured to measure a change in a property of the device in response to a change in the second bias potential.

17. The device of claim 1, wherein the electronic circuitry is configured to measure a change in sensitivity to glucose in response to a change in temperature in vivo.

18. The device of claim 1, wherein at least one of the first electrode or the second electrode comprises a thermally conductive core, and wherein the electronic circuitry is configured to measure a change in temperature of the thermally conductive core.

19. The device of claim 1, wherein at least one of the first electrode or the second electrode comprises a portion comprising a shape memory material, and wherein the electronic circuitry is configured to measure a pressure change of the shape memory material responsive to a temperature change in vivo.

20. The device of claim 1, further comprising a fiber optic sensor configured to measure a temperature in vivo, and wherein the fiber optic sensor is embedded within at least one of the first electrode or the second electrode or affixed to at least one of the first electrode or the second electrode.

21. The device of claim 1, wherein the device comprises a processor configured to use a priori sensitivity information.

* * * * *